(12) United States Patent
Miyamoto et al.

(10) Patent No.: US 7,935,927 B2
(45) Date of Patent: May 3, 2011

(54) METHOD AND APPARATUS FOR OBSERVING A SPECIMEN

(75) Inventors: Atsushi Miyamoto, Yokohama (JP); Maki Tanaka, Yokohama (JP); Hidetoshi Morokuma, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 437 days.

(21) Appl. No.: 12/110,443

(22) Filed: Apr. 28, 2008

(65) Prior Publication Data
US 2008/0237456 A1 Oct. 2, 2008

Related U.S. Application Data

(63) Continuation of application No. 11/651,031, filed on Jan. 9, 2007, now Pat. No. 7,365,325, which is a continuation of application No. 10/995,388, filed on Nov. 24, 2004, now Pat. No. 7,164,128.

(30) Foreign Application Priority Data

Nov. 25, 2003 (JP) .................................. 2003-393272

(51) Int. Cl.
*G01N 23/00* (2006.01)
*G01B 11/14* (2006.01)
(52) U.S. Cl. ..... 250/311; 250/306; 250/307; 250/491.1; 250/492.1; 250/310
(58) Field of Classification Search .................. 250/306, 250/307, 309–311, 396 R, 397–400, 396 ML, 250/491.1, 492.1, 492.2, 492.22, 492.3
See application file for complete search history.

(56) References Cited

U.S. PATENT DOCUMENTS

| 5,852,298 | A | 12/1998 | Hatakeyama | |
|---|---|---|---|---|
| 6,426,501 | B1 * | 7/2002 | Nakagawa | ......................... 850/5 |
| 6,614,026 | B1 | 9/2003 | Adamec | |
| 6,753,518 | B2 * | 6/2004 | Watanabe et al. | .......... 250/201.3 |

(Continued)

FOREIGN PATENT DOCUMENTS

JP        2000-348658        12/2000

(Continued)

OTHER PUBLICATIONS

"Characterisation of 193nm Resist Layers by CD-SEM Sidewall Imaging", Marschner et al, Proceedings of SPIE, vol. 5038 (2003).

*Primary Examiner* — Bernard E Souw
(74) *Attorney, Agent, or Firm* — Antonelli, Terry, Stout & Kraus, LLP.

(57) ABSTRACT

A method and device for observing a specimen, in which a convergent electron beam is irradiated and scanned from a desired direction, on a surface of a calibration substrate on which a pattern with a known shape is formed, and a beam SEM image of the pattern formed on the calibration substrate is obtained. An actual direction of the electron beam irradiated on the surface of the calibration substrate is calculated by use of the information about an apparent geometric deformation of the known shape on the SEM image, and the actual direction of the electron beam to the desired is adjusted direction by using information of the calculated direction. The pattern with the known shape formed on the calibration substrate has a crystal plane formed by anisotropic chemical etching.

23 Claims, 15 Drawing Sheets

U.S. PATENT DOCUMENTS

| | | |
|---|---|---|
| 6,765,647 B1 | 7/2004 | Nishi et al. |
| 6,852,974 B2 | 2/2005 | Kochi et al. |
| 7,164,128 B2 * | 1/2007 | Miyamoto et al. ............ 250/311 |
| 7,365,325 B2 * | 4/2008 | Miyamoto et al. ............ 250/311 |
| 7,476,882 B2 * | 1/2009 | Nakayama et al. ......... 250/492.3 |
| 2003/0218133 A1 | 11/2003 | Petrov |
| 2004/0262515 A1 * | 12/2004 | Motoi et al. .................. 250/306 |
| 2004/0262516 A1 * | 12/2004 | Motoi et al. .................. 250/306 |
| 2005/0116182 A1 * | 6/2005 | Tanaka et al. .............. 250/492.1 |
| 2005/0133718 A1 | 6/2005 | Miyamoto |
| 2007/0114398 A1 | 5/2007 | Miyamoto |
| 2009/0252402 A1 * | 10/2009 | Nagano ........................ 382/145 |

FOREIGN PATENT DOCUMENTS

| | | |
|---|---|---|
| JP | 2002-031520 | 1/2002 |
| JP | 2002-270126 | 9/2002 |
| JP | 2003-318099 | 11/2003 |
| WO | WO01/45136 | 6/2001 |

* cited by examiner

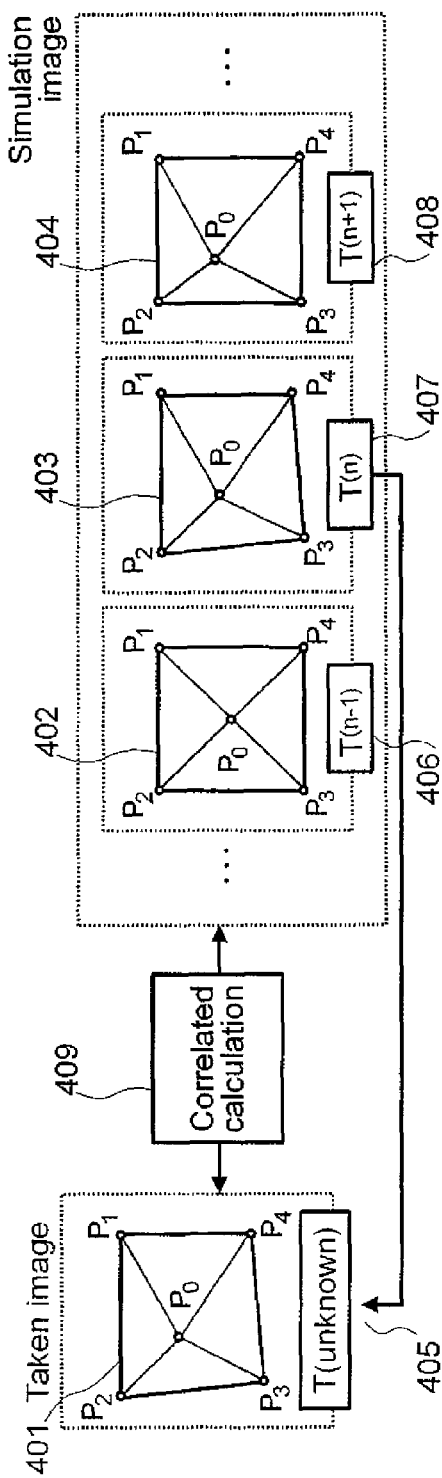
FIG.10
FIG.11
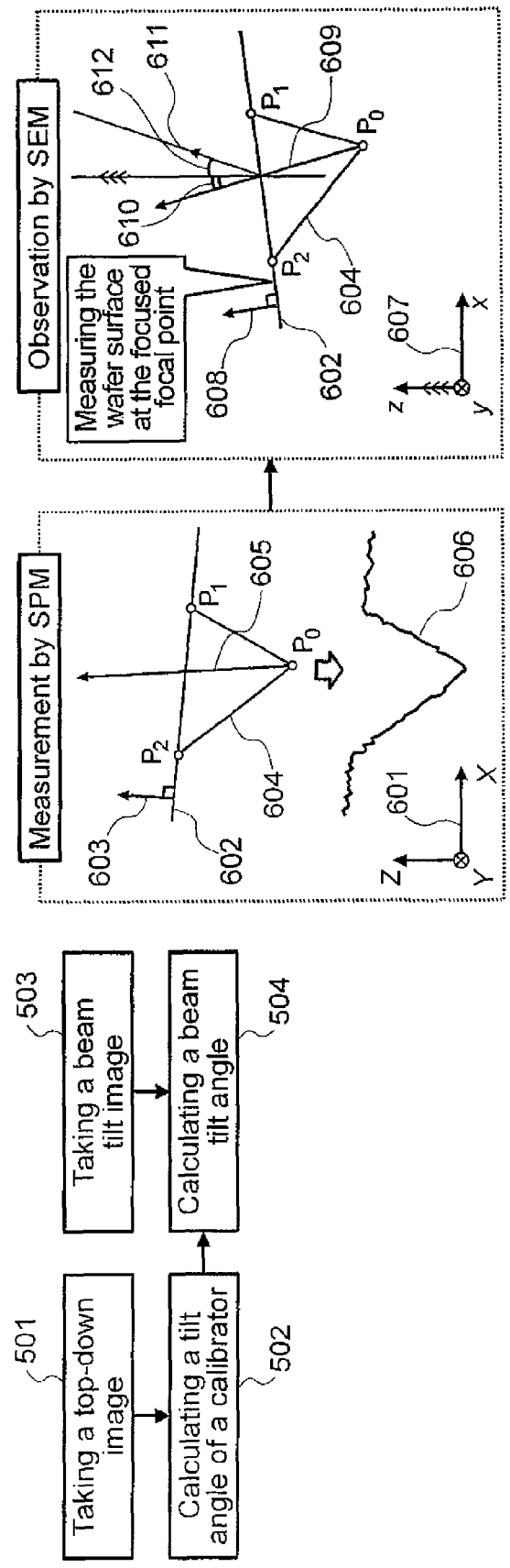
FIG.12

METHOD AND APPARATUS FOR OBSERVING A SPECIMEN

CROSS REFERENCE TO RELATED APPLICATION

This application is a continuation of U.S. application Ser. No. 11/651,031, filed Jan. 9, 2007, now U.S. Pat. No. 7,365,325, which is a continuation of U.S. application Ser. No. 10/995,388, filed Nov. 24, 2004, now U.S. Pat. No. 7,164,128, the contents of which are incorporated herein by reference.

BACKGROUND OF THE INVENTION

The present invention relates to a method and it's a device used to observe a specimen using a SEM (Scanning Electron Microscope) in the observance or measurement of a semiconductor wafer, etc in a process of semiconductor manufacture.

It is getting harder to control front-end semiconductor processing as a result of the increasing miniaturization of semiconductors. Subtle changes in pattern shapes, such as corner radiuses, as well as the heights, line widths, and sidewall gradient angles of the patterns of the semiconductors, make a significant impact on the electrical characteristics of semiconductor patterns. Therefore, a technology to detect the changes in a process and control a process by measuring the dimensions or shapes of a semiconductor during manufacture is needed. A technology to estimate a 3D profile from the observations of sidewalls or images obtained by an SEM (referred to as an "SEM image" hereinafter) of a semiconductor pattern is expected to effectively control a process. It is supposed that utilizing the information of the SEM images of a specimen observed in an oblique direction will be effective for observing the sidewalls or estimating 3D profiles.

The methods to obtain such SEM images observed in an oblique direction include, for example, a method to take a tilted image by deflecting an electron beam that is irradiated from an electron optical system and tilting the direction thereof so as to. irradiate the electron beam to an object of an observation, as described in the Japanese Published Unexamined Patent Application (abbreviated to JP-A, hereinafter) No. 2000-348658; a method to take an image by tilting the stage itself which is used to move a semiconductor wafer so that any given position of a semiconductor wafer can be observed by the SEM; and a method to tilt mechanically an electron optical system of the SEM itself.

However, it is expected that the direction of observation (or the incident direction) of an observed image actually obtained using conventional technologies may have some errors relative to the set values. Therefore, the error portion may affect the analysis of the observed image afterward. For example, an error in the direction of an observation becomes an issue because dimensional values are changed by the direction of an observation when detecting a process change by monitoring dimensions, such as line widths and contact hole diameters (see "Characterization of 193 nm Resist Layers by CD-SEM Sidewall Imaging", Proceedings of SPIE Vol. 5038, pp. 892-900, 2003). In the 3D profile reconstruction technology used for performing stereo measurement with images observed from multiple directions, the errors in the observational directions affect the errors of profiles estimated because profiles are estimated based on the observational directions of multiple SEM images and the disparities among multiple SEM images.

SUMMARY OF THE INVENTION

The object of the present invention is to provide a method and apparatus for observing a specimen. Specifically, the method and apparatus of the present invention permit an accurate measurement or observation by accurately estimating the observational direction of an obliquely observed image, calibrating the tilt angle based on the estimated observational direction, and using the observational direction as input information for the profile measurement.

In one aspect of the present invention, an electron beam is irradiated on a specimen having a known shape, electrons discharged from the surface of the specimen are detected, the incident direction of a convergent beam is estimated based on the geometric deformation of the specimen having a known shape by using an image of the intensity of the electrons detected, and the estimated observational direction is used to analyze the observed images afterward to allow high-precision measurements. The specimens with a known shape include specimens prepared by using materials having a crystal structure (the angle made by crystal planes constituting surfaces is known), specimens with a surface profile measured by a measuring means, such as a scanning probe microscope (SPM), or specimens having a pattern pitch accuracy which is guaranteed by using laser interferometry exposures.

In one aspect of the present invention, the actual observational direction can be matched to the set value by adjusting, for example, the polarization of an electron beam (referred to as "beam tilt" hereinafter), or the tilt angle of a stage or optical system itself (referred to as "stage tilt" or "body tube tilt" hereinafter) based on an estimated observational direction. In the 3D profile estimating technology, the accuracy of estimations can be improved by using the incident direction estimated as an input value of the observational direction of an observed image.

In a further aspect of the present invention, an estimated observational direction is displayed on GUI (Graphic User Interface) and is referred to when a user analyzes the observed images. A function to convert an image obtained by deflecting an electron beam into an image obtained by tilting a stage and displaying it based on the observational direction is offered. It is difficult to interpret a beam tilt image obtained by deflecting an electron beam intuitively, because it is geometrically different from an oblique perspective image as seen with the naked eye. Therefore, converting an image into a stage tilt image, which is comparable to observation by a human obtained by tilting a stage, is effective for analyses with the naked eye.

In another aspect, to accomplish the object described above, the present invention is directed to a method where a convergent electron beam is irradiated and scanned on a specimen, and a specimen is observed by a SEM image obtained by detecting the secondary electrons or reflected electrons generated from the specimen by the irradiation; a SEM image of the surface of a calibration substrate having a known pattern formed thereon is obtained by irradiating a convergent electron beam from an oblique direction on the calibration substrate and scanning it; an angle in an oblique direction of the electrons being irradiated is obtained by using information of a pattern with a known shape and the obtained SEM image; the obtained angle in an oblique direction is adjusted to a desired angle; a SEM image of the specimen substrate is obtained by irradiating an electron beam on the specimen substrate with a pattern formed from an oblique direction that is adjusted so that a desired angle in an oblique direction is obtained, and a 3D image or a cross-sectional shape of the specimen substrate is obtained by processing the SEM image by using information of a desired angle.

In still another aspect, to accomplish the object described above, the present invention is directed to a method where a convergent electron beam is irradiated and scanned on a specimen and the SEM image obtained by detecting the secondary electrons or reflected electrons generated from the specimen by the irradiation is used to observe the specimen; a SEM image of the surface of a calibration substrate having a known pattern formed thereon is obtained by irradiating a convergent electron beam from an oblique direction on the calibration substrate and scanning it; an angle in an oblique direction of an electron beam irradiated by use of the information of a known pattern shape and the SEM image is obtained; a SEM image of the surface of a calibration substrate having a known pattern formed thereon is obtained by irradiating a convergent electron beam from an oblique direction on the calibration substrate; a 3D image or a shape of a cross section of a pattern of the specimen substrate is obtained by processing the SEM image of the specimen substrate by use of the information of the angle obtained from the SEM image of a known pattern shape.

According to an aspect of the present invention, the observational direction is correctly estimated by using a specimen with a known pattern formed as a calibrator, thereby allowing more precise and repeatable measurements of shapes.

According to an aspect of the present invention, an observational direction is correctly estimated by using a specimen with a known pattern formed as a calibrator, thereby allowing the same results even if the same specimen is observed or measured with different devices.

These and other objects, features and advantages of the invention will be apparent from the following more particular description of preferred embodiments of the invention, as illustrated in the accompanying drawings.

BRIEF DESCRIPTION OF THE DRAWINGS

FIG. 10 is a schematic diagram of a method used to estimate a tilt angle;

FIG. 11 is a diagram showing an embodiment of an image acquisition sequence when estimating a tile angle;

FIG. 12 is a diagram showing an embodiment of a procedure to estimate a tilt direction of a calibrator by combining image processing, SPM and focused focal point measurement;

FIG. 18(a) is a perspective view of a pole-shaped specimen;

FIG. 18(b) is a perspective view of a hole-shaped specimen;

FIG. 18(c2) is a diagram of a hole-shaped specimen observed from above; and

FIG. 18(d) is a diagrammatic cross-section of a hole 1807 and a calibrator 1808.

DESCRIPTION OF THE PREFERRED EMBODIMENTS

The present invention will now be explained with reference to FIG. 1 to FIG. 17.

A Method to Observe Tilt with a SEM

Figure 1:
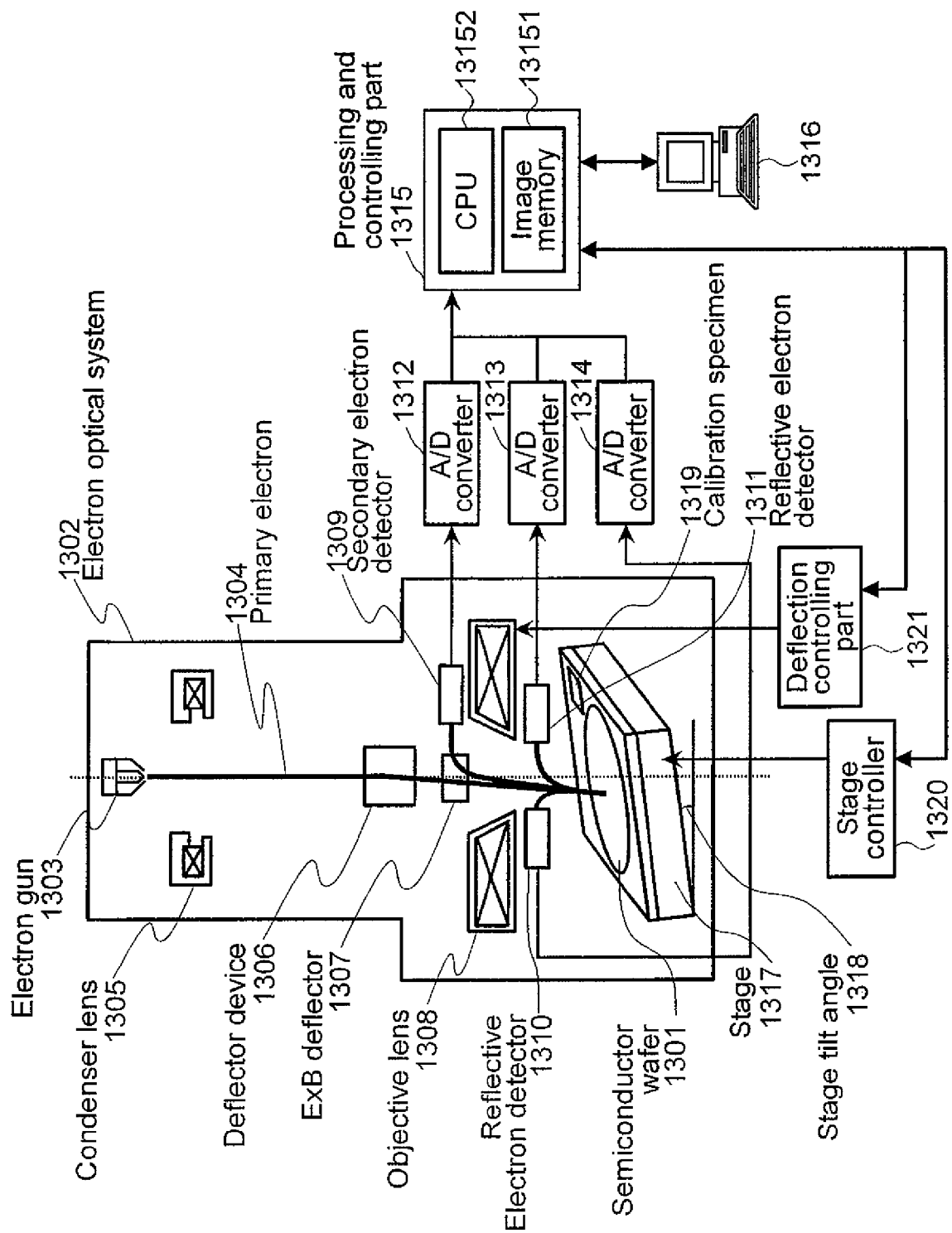
FIG. 1 is a diagram showing an embodiment of a system according to the present invention.

FIG. 1 shows an example of a system used to obtain and process a SEM image. An electron beam source 1303 generates an electron beam 1304. A deflector device 1306 deflects the electron beam 1304 to control the position at which the electron beam is irradiated on a specimen, such as semiconductor wafer 1301. The semiconductor wafer 1301 that is irradiated with an electron beam discharges secondary electrons and reflective electrons. The secondary electrons are detected with a secondary electron detector 1309. Meanwhile, reflective electrons are detected with the reflective electron detectors 1310 and 1311. The reflective electron detectors 1310 and 1311 are installed in different directions from each other. the secondary electrons and reflective electrons detected with the secondary electron detector 1309 and the reflective electron detectors 1310 and 1311 are converted into a digital signal using A/D converters 1312, 1313 and 1314; and, the digital signal is stored in an image memory 13151 and processed with a CPU 13152 depending on the purpose.

FIGS. 3(a) and 3(b) illustrate a method used to image a signal amount of electrons discharged from a semiconductor wafer when scanning an electron beam on the semiconductor wafer. An electron beam, for example, as shown in FIG. 3(a), is scanned and irradiated in the directions x and y as beams 1501 to 1503 or 1504 to 1506. The scanning direction of an electron beam can be changed by changing the deflecting direction of the electron beam. $G_1$ to $G_3$ indicate the respective points of electron beams 1501 to 1503 that are scanned in the direction x on a semiconductor wafer. In the same manner, $G_4$ to $G_6$ indicate the respective points of electron beams 1504 to 1506 that are scanned in the direction x on a semiconductor wafer. The signal amount of electron discharged at the points $G_1$ to $G_6$ has an intensity value corresponding to pixels $H_1$ to $H_6$ in an image 1509 shown in FIG. 3(b) (the subscripts from 1 to 6 attached to G and H correspond to one another). A coordinate system 1508 indicates the directions x and y in an image.

In FIG. 1, a computer system 1315 estimates an incident direction of a convergent electron beam from an observed image of a calibration specimen 1319 by performing image processing, estimates a 3D profile from an observational image of an object pattern on a semiconductor wafer 1301, or performs a processing and control, such as sending a control signal to a stage controller 1320 or a deflection controller 1321. A processor and controller 1315 is connected to a display 1316, and it has a GUI (Graphic User Interface) to display an image to a user. An XY stage 1317 moves the semiconductor wafer 1301, thereby allowing the semiconductor wafer to be imaged at any given position. FIG. 1 shows an embodiment with two detectors of a reflective electron image. It is possible to increase or decrease the number of detectors of the reflective electron image.

The methods for a SEM to observe an object that is tilted include (1) a method to take a tilted image by deflecting an electron beam irradiated from an electron optical system and tilting the direction to irradiate the electron beam, as disclosed in JP-A-2000-348658 (referred to as a "beam tilt method" hereinafter, and the image obtained is called a "beam tilt image"); (2) a method to tilt the stage 317 itself that moves the semiconductor wafer (in FIG. 1, the stage is tilted at a tilt angle 1318) (referred to as a "stage tilt method" hereinafter, and the image obtained is called a "stage tilt image"); and (3) a method to mechanically tilt the electron optical system itself (referred to as a "body tube tilt method", and the image obtained is called a "body tube tilt image". It is required to know the correct incident direction of a convergent electron beam in order to detect a process change and control a process by measuring a line width or a contact hole diameter, or for performing a precise analysis, such as an estimation of a 3D profile precisely from a SEM image obtained by the method. However, the current technology can not determine how much an actual incident direction is deviated from a set value of an incident direction of a convergent electron beam. Therefore, a method to correctly estimate the actual incident direction is needed.

A Basic Idea of the Present Invention

In order to solve the above-stated problem, the present invention has adopted a method to estimate an incident direction of a convergent electron beam by irradiating a convergent electron beam on a specimen with a known shape, detecting electrons discharged from the surface of the specimen, using an image of the intensity of the electrons detected, based on a geometric deformation of the specimen with a known shape on the image, to determine the incident direction. In other words, an incident direction (a tilt angle) of an electron beam is estimated on the basis of an orientation of the specimen with a known shape (a calibrator). If the orientation of a calibrator relative to an absolute coordinate system of an electron optical system can be measured, an incident direction of an electron beam to an absolute coordinate system of the electron optical system can be measured.

An absolute coordinate system of an electron optical system is a coordinate system having a z-axis oriented at an incident direction (a central axis of an optical system) of an electron beam at a beam tilt angle 0°, an x-axis orthogonal to the z-axis on a plane surface including electron beams 1501 to 1503 that are scanned in the x direction shown in FIG. 3(a), and, likewise, a y-axis oriented in a direction orthogonal to the z-axis on a plane surface including electron beams 1504 to 1506 that are scanned in the y direction.

If the orientation of a calibrator to an absolute coordinate system of an electron optical system can not be measured, an incident direction (it may be slightly different from a set value) of an electron beam to a coordinate system specified by some criteria (for example, a coordinate system with a z-axis oriented in an incident direction of an electron beam when a set value of a beam tilt angle is 0°) can be measured.

Figure 2:
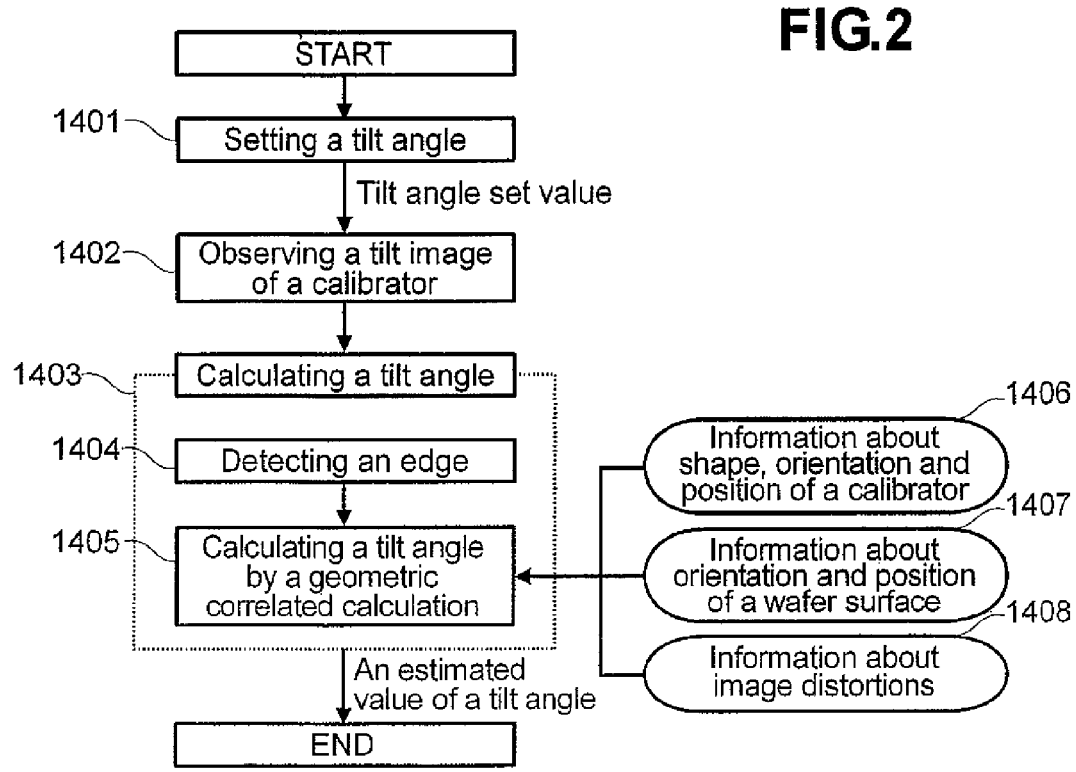
FIG. 2 is a flowchart showing the processing used to estimate a tilt angle.
Figure 3:
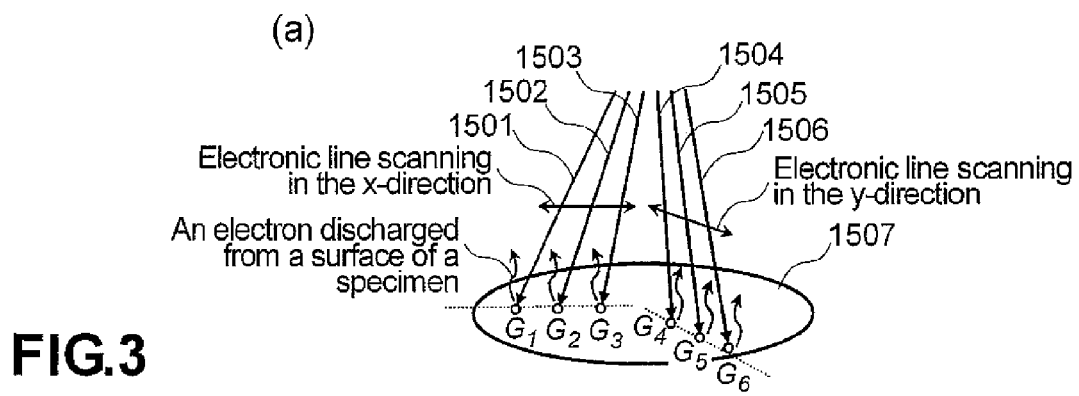
FIGS. 3(a) and 3(b) are diagrams showing a method to image the amount of a signal of electrons discharged from a semiconductor wafer.
Figure 3:
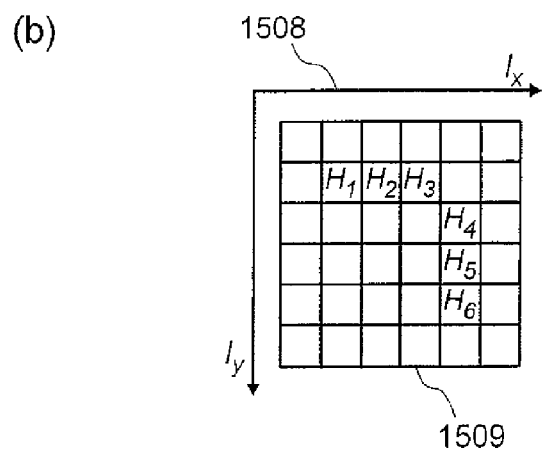

FIG. 2 shows a sequence used to estimate a tilt angle in accordance with the present invention. First, a beam tilt angle, a stage tilt angle or a body tube tilt angle of a device is set in a step 1401 (a beam tilt angle, a stage tilt angle and a body tube tilt angle are collectively named "a tilt angle" hereinafter). A calibrator is observed in a step 1402.

The calibrators used here include (1) a specimen utilizing a crystal plane (an angle made by crystal planes constituting a surface is known), (2) a specimen with a surface profile measured by a measuring means, such as a scanning probe microscope (SPM) or (3) a specimen with a pattern pitch accuracy guaranteed by using laser interferometry exposure.

In a step 1403, a tilt angle is estimated based on a geometric deformation of a calibrator on an observed image and a deviation of an incident direction of convergent electrons from a set value in the step 1401 is detected. The step 1403 is composed of the steps 1404 and 1405. A section where the tilt of the shape of a specimen changes significantly shows a difference in the appearance of a specific calibrator (a ridge or valley). This is called an "edge" hereinafter.

In a step 1404, an edge is detected in an observational image of a calibrator. In a step 1405, a tilt angle is estimated based on the geometric deformation on an observational image of the calibrator. At this moment, all or a part of the information concerning the shape, orientation and position of the calibrator 1406, the orientation and position of the wafer surface 1407 or the image distortion 1408 are required for estimating the tilt angle. Therefore, in the step 1405, as the tilt angle, a part or all of the information 1406 to 1408 is estimated based on the geometric deformation on an observational image of a calibrator, or a part or all of the information 1406 to 1408 is estimated by combining the distance measuring means using image processing, SPM or a focused focal point position on an objective lens, etc. In order to estimate a tilt angle, at least, the orientation of a calibrator should be known or estimated among the information 1406 to 1408.

An estimated tilt angle is used for (1) calibrating the tilt angle (matching a set value of a tilt angle to an actual tilt angle, (2) effecting improvement by using an estimated tilt angle as an input value to a stereo measurement, or (3) observing or measuring an observational image by displaying the tilt angle on a GUI (Graphic User Interface) for a reference of an observation and analysis of a user. The details of each step will now be explained.

A Calibrator with a Known Shape

Types of Calibrator

The specimens with a known shape that is used as a calibrator include, as mentioned above, (1) a specimen utilizing a crystal plane (an angle made by crystal planes constituting a surface is known), (2) a specimen with a surface profile measured by a measuring means such as a scanning probe microscope (SPM), (3) a specimen with a dimensional accuracy guaranteed by a pitch formation using laser interferometry exposure, or (4) a specimen that is usable for a standard.

The specimens of the type (1) will now be explained. Crystal anisotropy etching is a method used to constitute a specimen surface with a crystal plane. That is an etching technology using a property in which the etching rate differs from crystal plane to crystal plane. For example, in an Si crystal, the etching rate for a Miller's index plane (111) is much lower than the etching rate of a plane (100) or (110). Therefore, etching proceeds in such a manner that the plane 111 with a low etching rate comes to the top.

FIGS. 4(a) to 4(d) show examples of specimens constituted of Si crystal planes. A specimen with a Quadrangular pyramidal concave portion 101 (referred to as a "concave pyramidal type specimen" hereinafter), as shown in FIG. 4(a), is composed of a plane (111) and a planes (111) (111) (111) that have the direction of a plane equivalent to the plane (111). Therefore, a tilt angle between crystal planes is known. FIGS. 4(b), 4(c) and 4(d) show a specimen with a Quadrangular pyramidal convex portion 102 (referred to as "concave pyramidal type specimen"), an angle specimen 107 (tilt angle tan-1($\sqrt{2}$)°) and a line and space type specimen 108 (tilt angle 90°), respectively. Other than them, specimens using varied crystal, planes of not only Si crystals, but also GaAs crystals can be generated.

Variations of the pyramidal specimens include a pyramid sample with an upper portion (corresponding to the area around the vertex $P_0$ in FIG. 4(b)) of the pyramid being flat and a plane formed by vertexes $Q_5$ to $Q_8$, as shown in FIG. 5(a), a specimen that looks like a deformed pyramid with a round upper portion of a pyramid, or a deformed pyramidal specimen with an area (the area around $Q_0$-$Q_1$, $Q_0$-$Q_2$, $Q_0$-$Q_3$, $Q_0$-$Q_4$ in FIG. 4(b) on which planes constituting a pyramid are ground to be flat, as shown in FIG. 5(c).

The specimens of the type (2) will now be explained. Distance data is obtained by measuring a shape of a surface of a specimen with a measuring means, such as a SPM. The angles made by planes constituting the surfaces of the specimen are obtained through a polyhedral approximation by performing local plane applications. Any given specimens which are appropriate for observing a SEM image by the measurement method can be used.

The specimen of the type (3) will now be explained. The pitch of the pitch pattern is known because the exposure using an interference of a laser forms a pitch pattern with a high degree of accuracy.

Figure 18:
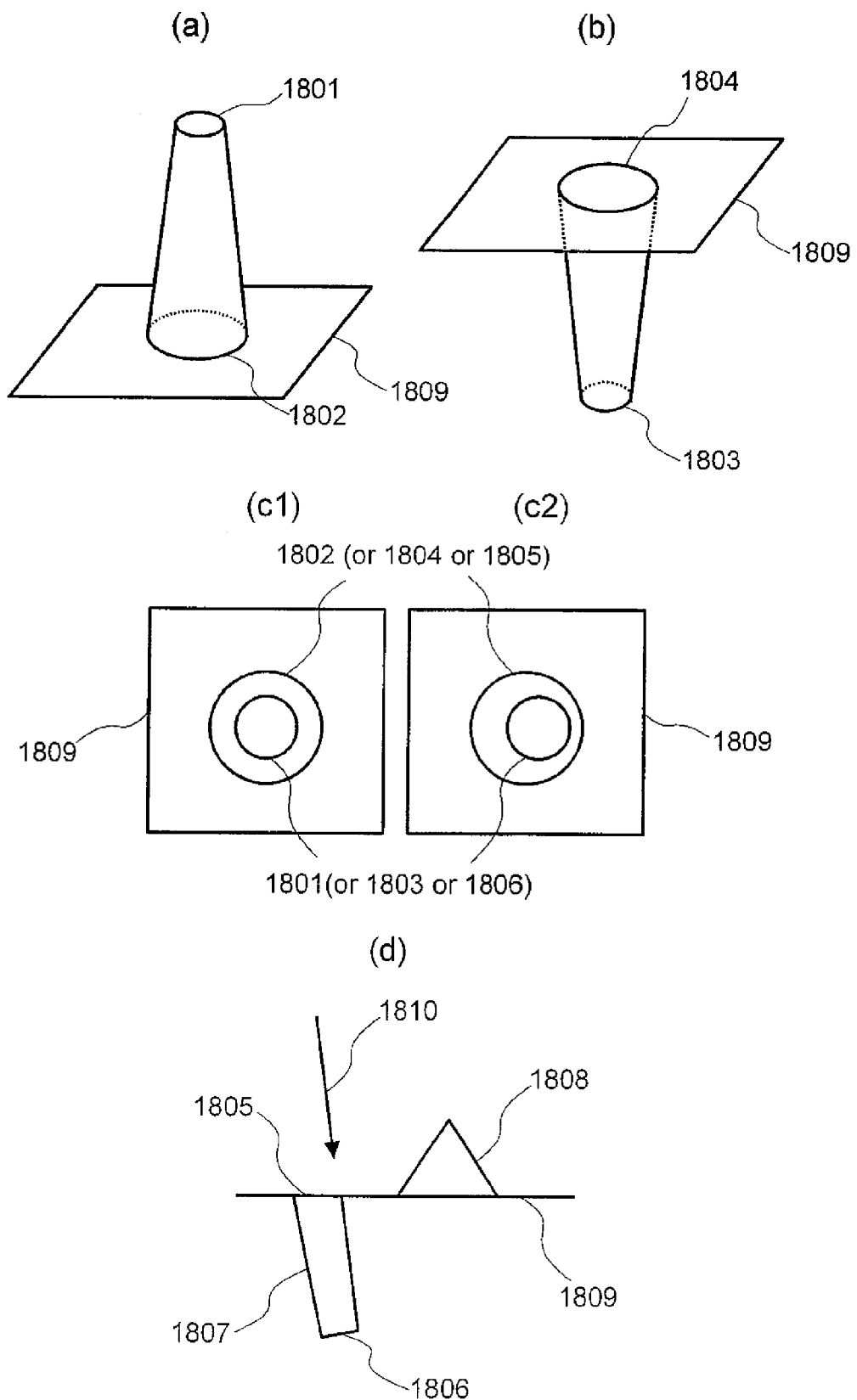
FIG. 18(c1) is a diagram of a pole-shaped specimen observed from above.

The specimens of type (4) will now be explained. For example, specimens of the pole and hole types shown in FIG. 18(a) and FIG. 18(b), respectively, can be used for a standard in the observational direction (the shapes where a section is getting larger or smaller towards the center axis direction of a pole or hole as shown in the drawings are included). FIG. 18(c1) and FIG. 18(c2) are examples of observational images of FIG. 18(a) and FIG. 18(b) observed approximately from above. For example, when the hole of FIG. 18(b) is opened perpendicular to a wafer upper surface 1809, if the center locations of the upper surface 1804 and the lower surface 1803 of the hole are matched to each other in an observed image, as shown in FIG. 18(c1), the observational direction is judged to be perpendicular to a wafer. In other words, it can be used as a standard in the observational direction. An observational direction can be judged vertically with a higher resolution if a hole is deep because the center location s of the upper surface 1804 and the lower surface 1803 of the hole are deviated relative to each other, as shown in FIG. 18(c2), even when the observational direction is slightly deviated from the vertical direction.

Specimens including a sharp tilt typified by the pole or hole type are advantageous because the specimen can be confined in a visual field, the resolution is high and the range of changes in height in the z-direction of a calibrator is large. In addition, the deviation from the vertical direction of an observational direction can be estimated by a geometric relationship with a deviation of the center location. Further, an observational direction can be calibrated in the vertical direction by including the center location. Further again, if a hole is bored in any given direction relative to the upper surface of a wafer, it is possible to judge whether the observational direction is the given direction, to estimate the amount of deviation of an observational direction and the given direction or to calibrate an observational direction relative to the given direction.

If the direction of a hole bored is once cleared by a measurement, etc, after that, it can be used as a standard for the direction of the hole bored. Also, in the pole type specimens, as a specimen of the above mentioned hole type, it is possible to judge, estimate or calibrate an observational direction.

In addition, an observational direction that can be judged, estimated or calibrated with any given standard typified by the pole or hole type also can be measured with any given calibrator. In other words, as an example shown in FIG. 18(d), in an observational direction where the center location of the upper surface 1805 of a hole 1807 is aligned to that of the lower surface 1806 of the same, as shown in FIG. 18(c1), for example, the direction of the tilt (an observational direction that can be judged, estimated or calibrated with a standard) of the hole 1807 can be obtained by observing the pyramidal calibrator 1808 and estimating the observational direction.

With regard to the definition of beam a tilt angle of 0°, the z-axis direction in an absolute coordinate system where the central axis of the optical system is the z-axis may be set to 0°. Or, any given vertical direction in appearance relative to a wafer surface or any given observational direction defined with a standard, etc also may be set to 0°.

An observational direction is estimated based on the differences in the appearances of the specimens by considering differences in the observational directions. For estimations of observational directions described below, something characteristically indicates a geometrical shape of a specimen on an observed image, such as the length or tilt angle of the segment 301 to 308 of the concave pyramid shown in FIG. 6(a), or a part or all of the coordinate value of the vertexes $P_0$ to $P_4$ shown in FIG. 6(a) should be detected and utilized (the vertexes $P_0$-$P_4$ correspond to R1-R6 in FIGS. 4(a)-4(d) and FIGS. 6(a)-6(e)). The segments correspond to the "edge" where the slope of the shape of a specimen changes significantly. They are segments 309 to 311 etc in a specimen of the line and space type as seen in FIG. 6(b).

A method to detect an edge from an observed image through image processing will now be described. For an observed image, either a secondary electron image taken from a signal amount detected with the secondary electron detector 1309 or a reflective electron image taken from a signal amount detected with the reflective electron detectors 1310 and 1311 is used.

In a secondary electron image, a difference in the slope of the shape of a specimen is reflected in a difference in the signal amount. In addition, a phenomenon called "edge effect" is observed at an edge part where the slope of the shape of a specimen changes significantly. A large signal amount is detected in an angular shape. On the contrary, a small signal amount is detected in a volley shape. Thus, an edge can be detected by detecting a part with a signal amount changing or a part of a peak with a large or small signal amount.

Also, in an image of a reflection electron, a difference in the slope of the shape of a specimen is reflected in a difference in the signal amount. Therefore, an edge can be detected by detecting an area with signals that are changing on an image. In a reflective electron image, the edge effect does not occur. Therefore, in some cases, it is desirable to use an image of a reflective electron to improve the accuracy of detecting an edge if an edge is observed that is much expanded due to the edge effect.

Each segment of a calibrator can be detected by detecting several areas where an edge with the slope of the shape of the specimen is significantly changed on a segment to be detected or there around and by applying a straight line to them. The detection of a segment 304 in the pyramidal specimen shown in FIG. 6(*a*) will now be explained by with reference to FIG. 6(*a*2), where an area 324 enclosed with the dotted lines in FIG. 6(*a*) is enlarged. Several edges are detected on the segment 304 or the around in FIG. 6(*a*2) corresponding to the area 314 in FIG. 6(*c*).

Black dots 321 indicate positions of multiple edges detected at any given interval along the segment 304. In some cases, the multiple positions where an edge is detected deviate and do not exist on a line due to the noises of images, etc. However, a straight line (i.e., segment 304) can be accurately detected by applying a straight line to the multiple positions 321 of edges by means of the least-square method, etc. to reduce the effect of the noise. However, if a large exceptional value with a propensity that is different from other points is included in the edge position 321 (for example, an edge position 322 spaced far apart from the straight line), a processing not considering an exceptional edge position can be selected by excluding an exceptional edge position that is spaced far apart from a detection line, or by performing a least-square method with each edge position weighted so as to be inversely proportional to the distance from a detection line of the edge position because a value estimated by the least-square method possesses lower reliability.

For example, when detecting the edge position 321, the approximate position of the segment 304 known in advance is convenient for use in finding an approximate detection range or detection direction, etc. Therefore, the approximate position of the segment 304 is determined before detecting the edge position 321 by a detection processing which is described below by way of example. At first, an entire image is differentially filtered to extract an approximate probable position of an edge from the image. An approximate position of each segment is estimated among points obtained by binarizing the output values of a differential filter by means of the Hough transform, which is commonly known as a voting-type line detection method.

Some geometric shapes of calibrators include a circular pattern, as shown in FIGS. 18(*a*) and 18(*b*). It is possible to express a geometrical shape quantitatively by applying a circular or curved pattern to an edge detected in the same manner as a straight line, or directly using a coordinate of an edge.

Advantages of Using Pyramid Specimens

A pyramidal (quadrangular pyramidal shape) has the following advantages when detecting these segments in a SEM image by image processing.

(1) Both sides of the edge of the specimen are symmetrical. Therefore, the distribution of the signal amount in an observed image is also symmetrical. Therefore, it is possible to detect an edge in an observed image with a high degree of accuracy.

(2) It is possible to estimate a two-dimensional(x and y direction) observational direction by observing a pyramid.

Figure 4:
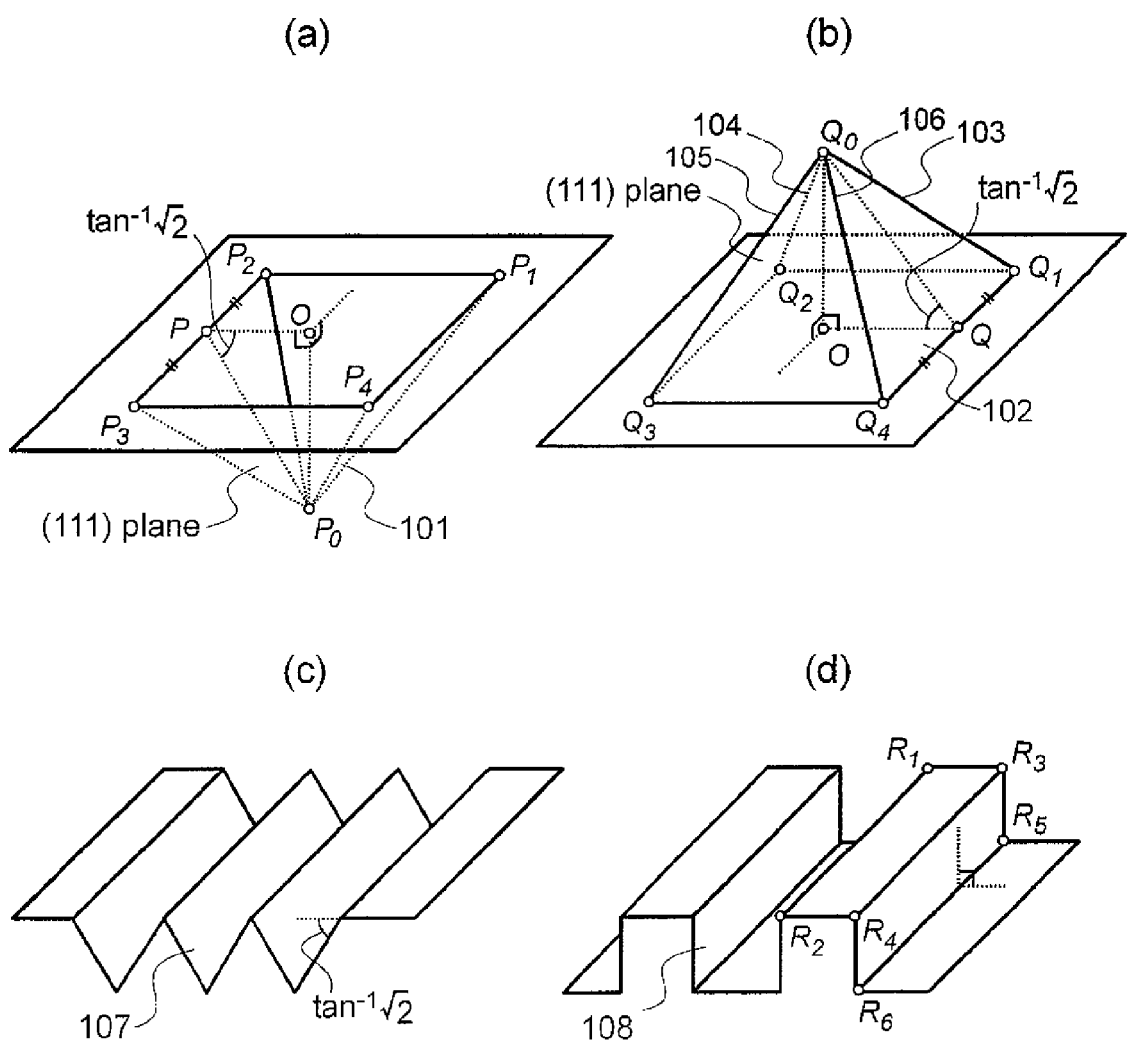
FIGS. 4(a) to 4(d) are diagrams showing a variation of a specimen using a crystal surface of an embodiment of a calibrator having a known shape.

With regard to item (1) mentioned above, FIG. 6(*c*) shows the distribution 312 of the amount of the SEM signals at the segment A-B in a concave pyramid and the distribution 313 of the shape of the surface of a specimen. Both sides of the position 314 of the straight line 304 to be detected are substantially symmetrical. Therefore, the distributions of the amount of the signals are also symmetrical. Because the deviation of the signal amount to one side is small, the position of a straight line that is close to the true value can be detected. The same propensity is observed in an angle specimen where either side of a straight line to be detected on the surface of the specimen is symmetrical, as shown in FIG. 4(*c*). This propensity is not significantly lost if the observational direction changes only slightly.

Figure 6:
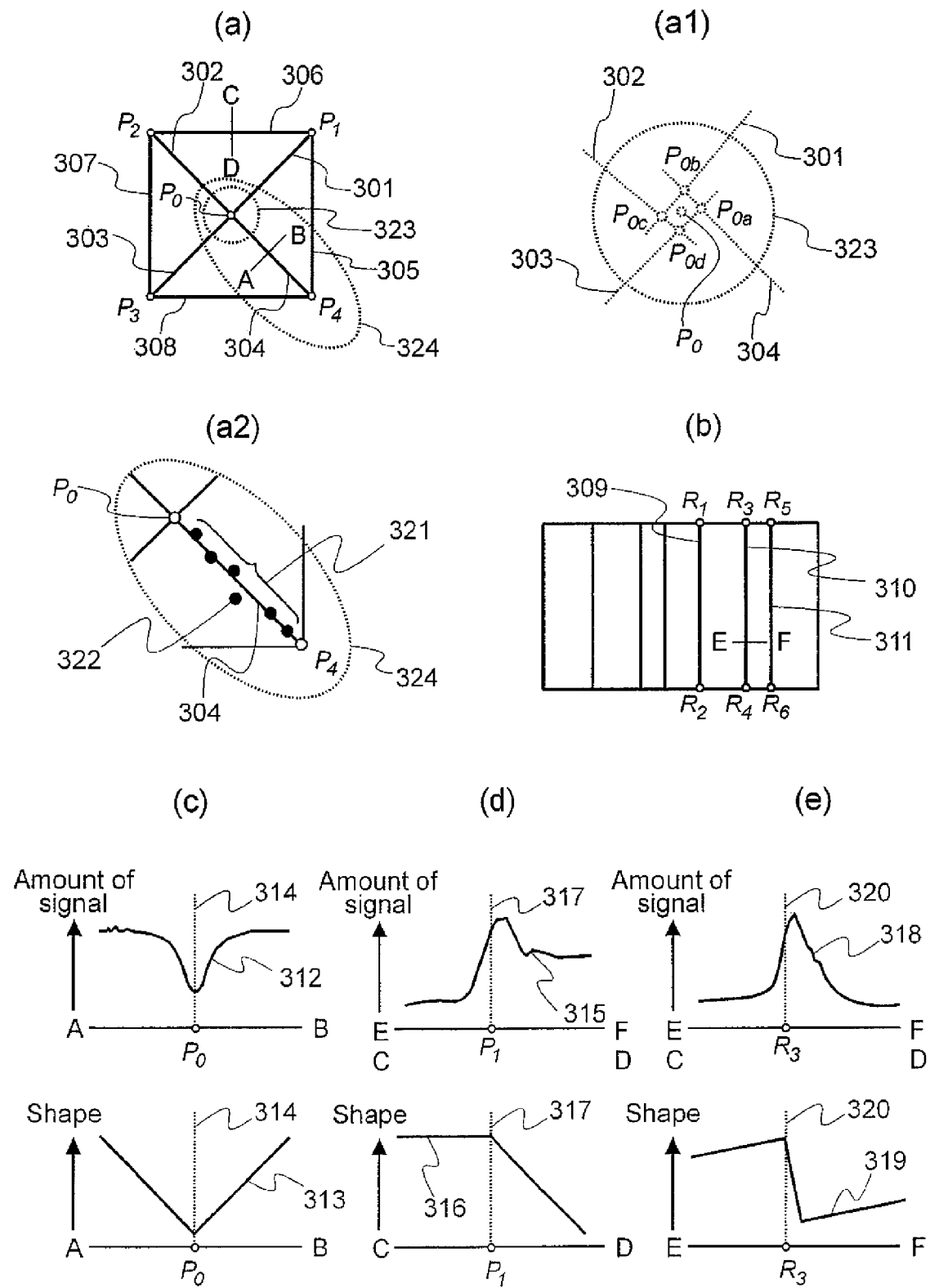
FIGS. 6(a) to 6(e) are diagrams which show an image of a calibrator, the distribution of the intensity in the observed image of the calibrator and a method to detect a segment.

Meanwhile, FIG. 6(*e*) shows the distribution 318 of the SEM signal amounts at the straight line E-F and the distribution 319 of the shape of the surface of a line and space type specimen. Because the shape on either side of the position 320 on the straight line 310 to be detected is different, the distribution of the signal amount on either side is also different resulting in a propensity of the signal amount to deviate on either side. Therefore, the detected position is in danger of deviating from a true value. However, if the signal amount deviates largely, it is possible to correct the deviation of the signal amount and improve the detection accuracy by estimating the distribution of generated signals expected from the shape of a specimen by the Monte Carlo simulation, etc.

If an observational direction is estimated by detecting the coordinate value of the vertexes $P_0$ to $P_4$ shown in FIG. 6(*a*), for example, an vertex may be obtained from an intersecting point of the straight lines detected. For example, the vertex $P_0$ and the vertex $P_1$ can be obtained from an intersecting point by a combination of a part or all of the straight lines 301 to 304, and a combination of a part or all of the straight lines 301, 305 and 306, respectively. FIG. 6(*a*1) shows an example of the vertex $P_0$ detected, where the area 323 enclosed by a dotted line in FIG. 6(*a*) is enlarged. When estimating a vertex from three or more straight lines in FIG. 6(*a*1), in some cases, the intersecting points $P_{0a}$ to $P_{0d}$ detected respectively from an intersecting point of the two straight lines arbitrarily selected may not meet one another. In this case, the deviation in detecting straight lines can be reduced by using the centroid or median point of the multiple intersecting point for the vertex $P_0$.

Figure 5:
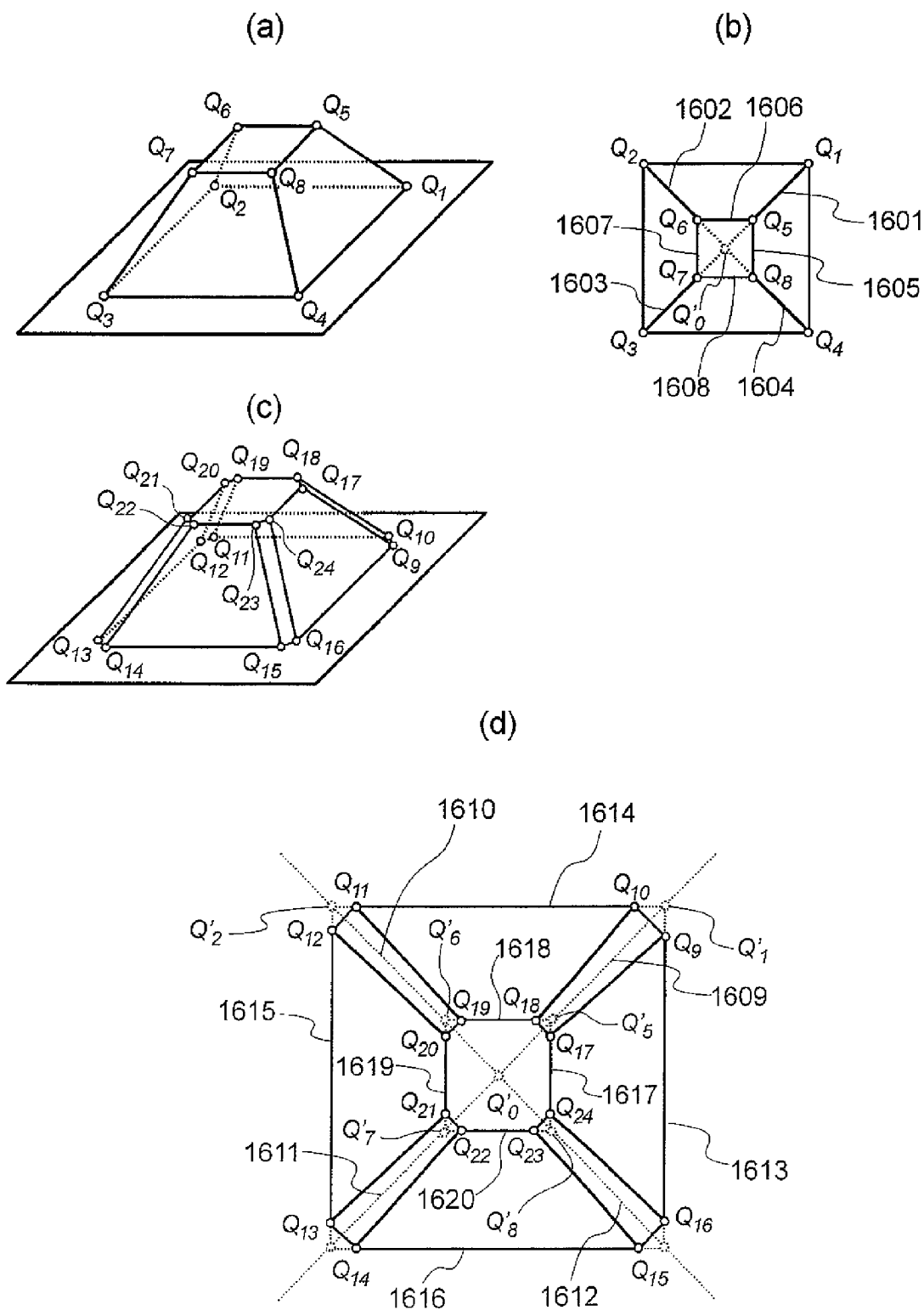
FIGS. 5(a) to 5(d) are diagrams showing a deformed example of a pyramid specimen of an embodiment of a calibrator having a known shape.

FIG. 5(*b*) shows the specimen of FIG. 5(*a*) when observed in a direction perpendicular to the wafer surface. With regard to a deformed specimen in a pyramidal shape having a flat upper portion, the geometric deformation of a pyramid on an observed image can be estimated by detecting the vertexes $Q_5$ to $Q_8$ or the segments 1605 to 1608 whose equivalents do not exist in the convex pyramid in FIG. 4(*b*). Meanwhile, the geometric form of this deformation also can be expressed by the vertexes or segments of normal pyramidal specimens. In other words, a geometric deformation of a pyramid can be estimated by extending the segments 1601 to 1604, respectively, and by detecting a virtual vertex $Q'_0$ corresponding to the vertex $P_0$ in FIG. 6(*a*) from the intersecting point. (The vertex $Q'_0$ can be detected by the same center-of-mass calculation as that of FIG. 6(*a*1)). It is possible to perform an analysis which is the same as that for the normal pyramid shown in FIG. 6(*a*) by using the virtual vertex $Q'_0$.

As shown in FIG. 5(*c*), in a specimen where an edge on which two planes constituting a pyramid meet each other is cut off so as to provide flat surface, there is a method to use a segment that does not exist in a normal pyramidal specimen as a characteristic of the shape. For example, a virtual vertex $Q'_1$ corresponding to the vertex $P_1$ in a normal pyramidal specimen as seen in FIG. 6(*a*) can be detected by extending the segments 1613 to 1614, respectively, and calculating an intersecting point. Further, the virtual straight line 1609 corresponding to the straight line 301 in FIG. 6(*a*) can be detected by extending the segments 1617 to 1618, detecting the virtual vertex $Q'_5$ (corresponding to the vertex $Q_5$ in FIG. 6(*a*)), and producing a line from the virtual vertex $Q'_1$ to $Q'_5$. Further, the virtual vertex $Q''_0$ corresponding to the vertex $P_0$ in FIG. 6(*a*) can be detected from an intersecting point made by a combination of a part or all of the virtual straight lines 1610 to 1612 detected in the same way as the virtual straight line 1609. It is possible to perform an analysis which is the same as that for the normal pyramids shown in FIG. 6(a) by using the virtual straight lines 1609 to 1612 or virtual vertex $Q''_0$.

With regard to the item (2) mentioned above, it is possible to estimate a two-dimensional observational direction by observing a pyramid because the slopes in the x- and y-observational direction of a pyramidal specimen are both expressed in accordance with the displacement of the vertex of the pyramid. Meanwhile, in the angle specimen and the line and space type specimen shown in FIG. 4(c) and 4(d), respectively, the changes in the observational direction without an edge (e.g., the direction from the vertexes $R_1$ to $R_2$ in FIG. 4(d)) can not be estimated. However, it is possible to estimate a two-dimensional observational direction by disposing multiple specimens in such a manner that the directions of the edges are different from each other (e.g., the example of disposition 709).

Size and Disposition of Specimens

The size and disposition of specimens will now be explained with reference to an example of a pyramidal specimen.

The size of a specimen should be so determined that (1) it is contained in the visual field when imaging, (2) it can observe a sufficient length of segment to secure a detection accuracy of each segment of a pyramid, and (3) it has a sufficient height to raise the resolution of the displacement of a pyramid on an image detected when the observational direction changes. The appropriate size of a pyramid is about 0.1 micrometer to a few micrometers in the case, for example, when the imaging magnification and focal depth are 30 k to 150 k and a few micrometers, respectively, depending on the imaging magnification and focal depth of the SEM.

The location and method which are employed to dispose a specimen will now be explained. The positions 704 and 705 in FIG. 7(a) are the candidate sites to install a specimen. The specimen is attached to position 704 on the semiconductor wafer 702 (corresponding to 1301 in FIG. 1), which is installed on the stage 701 (corresponding to 1317 in FIG. 1), or it is attached to position 705 on the holder 703, which is installed on the stage 701. In order to attach a specimen on position 704, it is required to prepare a wafer that is dedicated for a calibration where a calibrator is formed instead of the semiconductor wafer 702 and to attach it instead of the semiconductor wafer 702 or to attach the semiconductor wafer 702 that is provided with a calibration pattern when forming a semiconductor pattern.

In general, it is difficult to generate a calibration pattern, such as a pyramid, simultaneously with the semiconductor pattern. However, it is also possible to measure the semiconductor pattern generated on the semiconductor wafer 702 with a measuring means, such as a SPM, and to use it as a calibrator with a known shape. In addition, as shown in 704, the distortion of the stage or distribution of changes in the observational direction inside the plane caused by changes in the electric field due to the movements of the stage can be measured by disposing several specimens (nine specimens are used in position 704) leaving a space among them. Examples for disposing calibrators at position 704 or 705 will now be explained with reference to FIG. 7(b).

In the example 706 of the disposition shown in FIG. 7(b), pyramids 710 (corresponding to 101 or 102 in FIG. 4) of a predetermined size are disposed at a regular interval. Disposing multiple pyramids has the advantages of being able to (1) estimate the observational direction of each pyramid, use the average or median of the observational direction and reduce the deviation of the estimated values in the observational direction caused by the individual differences and image noises, (2) observe multiple pyramids in a single visual field and measure the distribution inside the visual field in the observational direction, and (3) observe other specimens when some specimens are contaminated and keep on favorable calibrations.

Further, as shown in FIG. 7(c), a distortion of an image in a visual field can be estimated and corrected by observing multiple pyramids with a known disposition (disposed in a reticular pattern in FIG. 7(c)) in a single visual field. In other words, (1) the scanning direction (corresponding to the x- and y-direction in an image) of a convergent electron beam is changed, or (2) a distortion of an image is corrected by re-configuring an image without any distortion by geometrically deforming an obtained image so that the line A-B originally forming a straight line connecting the vertexes of the pyramids in FIG. 7(c) is converted in the straight line C-D. A distortion of an image inside a visual field can be estimated and corrected by observing a single pyramid. In other words, for example, if the segments 301 to 308 of the concave pyramid in FIG. 6(a) are guaranteed to be straight, and the segments 301 to 308 are observed to be curved (e.g., an observed image of a concave pyramid in FIG. 7(d)), it is possible to adopt a distortion correcting means to correct the curved line to a straight line. If this kind of observed image is distorted significantly, it is necessary to correct the distortion of the observed image in order to estimate a tilt angle with a high degree of accuracy.

A method has been proposed to correct a distortion between the beam tilt images with different tilt angles by matching the bottom shapes of pyramids among images. In other words, focusing attention on a property that is specific to the beam tilt images in which the shape of the geometric pattern on a horizontal plane is stable against the x- and y-plane of an electron optical system irrespective of the beam tilt angle in the beam tilt images, for example, if a wafer surface is horizontal to the x- and y-plane of an electron optical system, the bottom shape of a pyramid on a wafer surface is stable irrespective of the tilt angle. Therefore, it is assumed that the difference in the shape among the beam tilt images is caused by a distortion in imaging. Consequently, the information about parameters used to express the images, segments, vertexes or shapes obtained without any distortions is obtained by correcting the parameters (e.g., gradient angle of the segments) expressing the images, or segments, vertexes or shapes of a pyramid detected in such a manner that the bottom shapes of pyramids match among images. In other words, it is possible to obtain an observed image with less distortion and estimate an observational direction with a high degree of accuracy.

Figure 8:
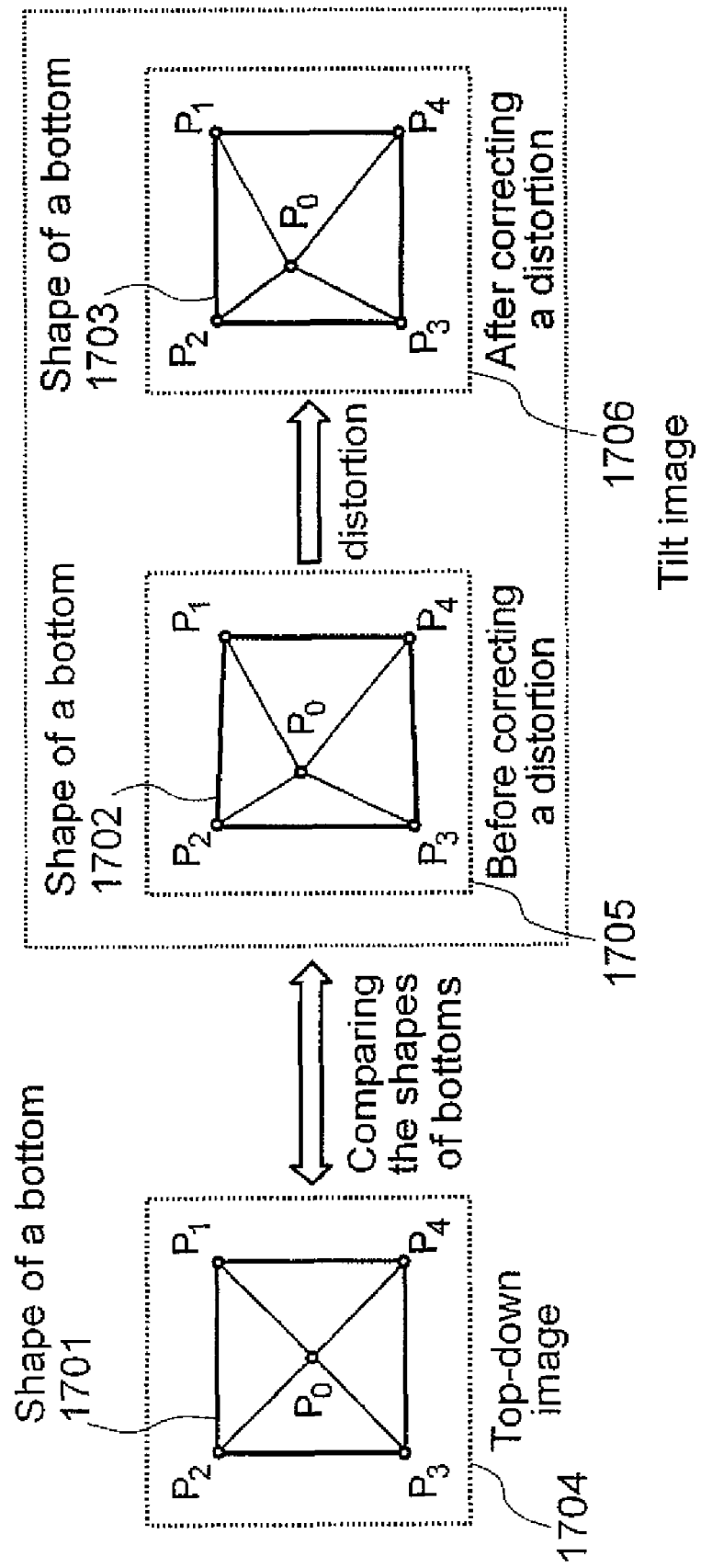
FIG. 8 is a diagram showing an example an illustration of strain compensation of an image.

FIG. 8 shows an example of the distortion correction processing used to match the bottom surface shape of a beam tilt image to the bottom surface shape of the top-down image on the basis of the bottom surface shape of a top-down image. The bottom surface shapes usable for a standard include a bottom surface shape obtained from a top-down image, a bottom surface shape obtained from a beam tilt image observed by any given beam tilt angles, or an average bottom surface shape obtained from multiple images in the same or different observational directions. In many cases, a top-down image has less image distortion than a beam tilt image. Therefore, a bottom surface shape obtained from a top-down image or an average bottom surface shape obtained from multiple top-down images is often effective.

The bottom shape 1701 in FIG. 8 (lines sequentially connecting vertexes $P_1$ to $P_4$) is a bottom surface shape in the top-down image 1704. A deformation parameter to correct the bottom shape 1702 in beam tilt image 1705 to match the shape 1701 is obtained. A beam tilt image 1706, after distortion correction, is obtained by correcting a distortion of the beam tilt image 1702 with the deformation parameter. The bottom shape 1703 in the beam tilt image 1706 after distortion correction is more similar to the bottom shape 1701 than the bottom shape 1702.

Figure 7:
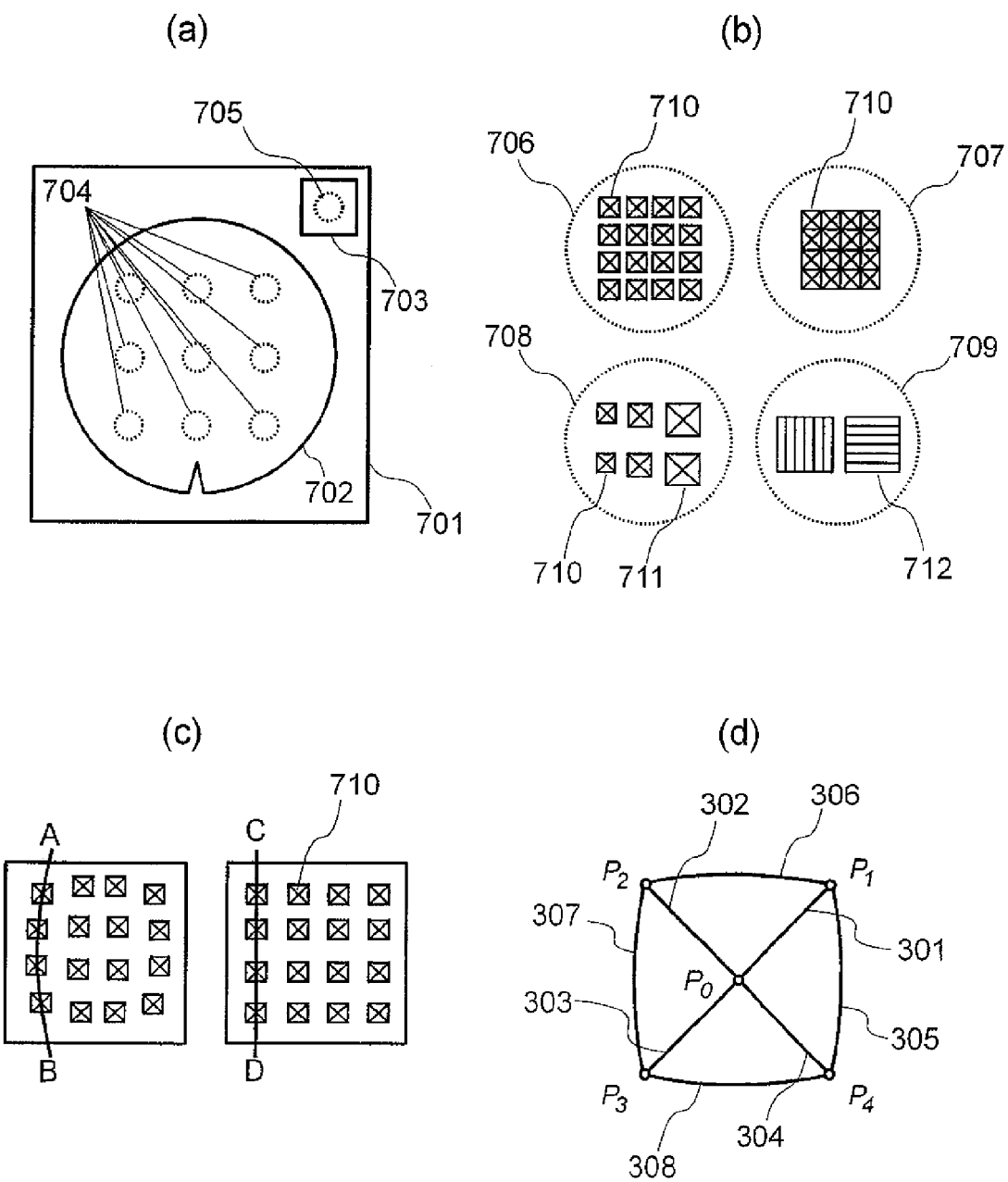
FIGS. 7(a) to 7(d) are diagrams which show variations of arrangements of a calibrator.

In the disposition example 707, as seen in FIG. 7(*b*), the pyramids 710 having the same size are arranged without intervals among pyramids. The advantages in such an arrangement include a measurement allowed in the same manner as the disposition example 706, and substantially the same distribution of the SEM signal amount of the bottom of a pyramid (segments 305 to 308 in FIG. 6(*a*)) at the both sides of a bottom to be detected. In other words, in the disposition example 706, the distribution of the SEM signal amount at the line C-D, as shown in FIG. 6(*a*), is likely not to be symmetrical at both sides of the position 315 of the bottom 306, as shown in FIG. 6(*d*). However, in the disposition example 707, the distribution is substantially symmetrical, allowing a position of a straight line near the true value to be detected.

In the disposition example 708, as seen in FIG. 7(*b*), multiple pyramids having different sizes (for example 710 and 711) are disposed. If the size of the visual field changes due to changes in the imaging conditions, it is possible to select and observe pyramids with an appropriate size to secure an estimated accuracy of an observational direction.

The above-mentioned examples of dispositions can be applied to the angle specimen 107 and the line and space type specimen 108 shown in FIG. 4(*c*) and FIG. 4(*d*), respectively. Further, in the angle specimen 107 and the line and space type specimen 108, the two-dimensional (x- and y-direction) observational directions can be estimated by disposing a calibrator 712 (corresponding to 107 or 108) in such a manner that the rolls of the shape of the specimen are bidirectional, as in the example of the disposition 709 shown in FIG. 7(*b*).

Tilt Angle Estimation Method

Figure 9:
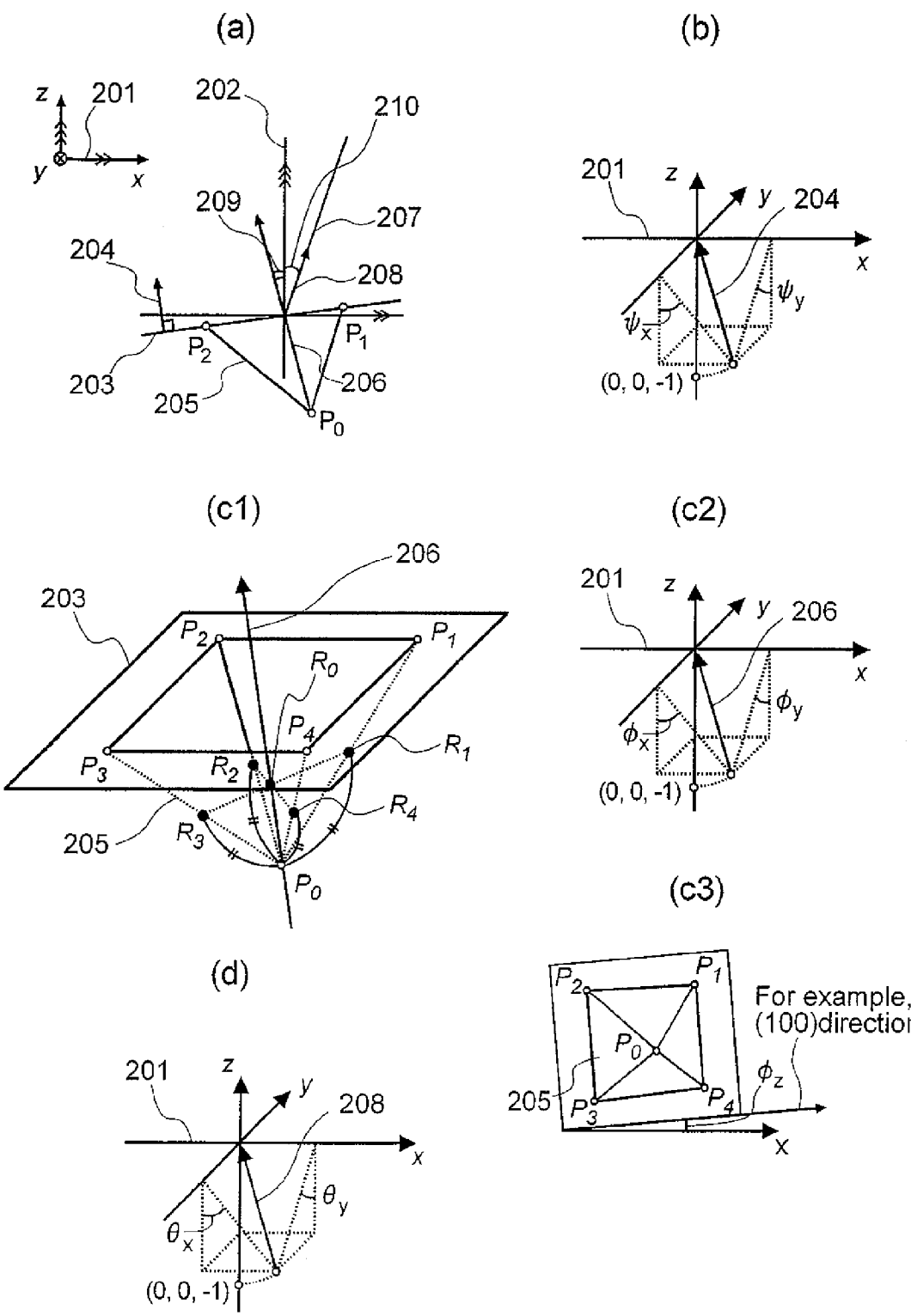
FIGS. 9(a) to 9(d) are diagrams which show an illustration of the positional relationship among the wafer surface, calibrator and incident direction of an electron beam.

Definition of Relationship Among Wafer Surfaces, Calibrators and Incident Directions of Electron Beams A method of estimation of the beam tilt angle by SEM observation using the beam tilt method will now be explained with reference to a concave pyramidal specimen used as a calibrator. FIG. 9(*a*) is a pattern diagram showing the positional relationship among a wafer surface 203, a pyramid 205 (a calibrator), and an incident direction 207 of an electron beam, when a concave pyramidal type specimen is observed. The wafer surface is means an area where no pyramid is formed on a surface of a specimen having a pyramid formed thereon. It is different from a semiconductor wafer used to form a semiconductor pattern actually being analyzed. An example of a method used to describe the wafer surface, pyramid and incident direction of an electron beam will now be explained. The absolute coordinate system 201 of the electron optical system is used for a standard of the positional relationship.

First, the slope of the wafer surface 203 shown in FIG. 9(*a*) can be expressed with the unit surface normal vector 204 of the wafer surface. The unit surface normal vector 204 can be expressed as FIG. 9(*b*) by using the rotation $\psi y$ and $\psi x$ around the x- and y- axis of the unit surface normal vector 204 relative to the absolute coordinate system 201.

Then, the slope of the concave pyramid 205 shown in FIG. 9(*a*) can be expressed with the unit orientation vector 206 of the center axis of the concave pyramid.

The unit orientation vector 206 can be expressed shown in as FIG. 9(*c2*) by using the rotation $\phi y$ and $\phi x$ around the x- and y-axis of the unit orientation vector 206 relative to the absolute coordinate system 201. The central axis of the concave pyramid is a reference axis used to uniquely define the orientation of a pyramid. For example, as shown in FIG. 9 (*c1*), it is the straight line 206 connecting the points with the same distance from each edge $P_0$-$P_1$, $P_0$-$P_2$, $P_0$-$P_3$ and $P_0$-$P_4$ of a pyramid. The relative angle between the slope of the wafer surface and the slope of the pyramid is known if the wafer surface 203 is a (100) crystal plane. In addition, with regard to the rotation of the concave pyramid 205 (rotation of the crystal orientation) in FIG. 9(*c3*), the angle of the projection vector of the wafer crystal orientation (100) vector on the x- and y-plane with the x-axis can be expressed as $\phi z$.

Then, the incident direction 207 of an electron beam 207 shown in FIG. 9(*a*) can be expressed with the unit orientation vector 208 in the incident direction of the electron beam 207. The unit orientation vector 208 can be expressed as shown in FIG. 9(*d*) by using the rotation $\theta y$ and $\theta x$ around the x- and y-axis of the unit orientation vector relative to the absolute coordinate system 201.

It is required to estimate a part or all of the parameters $\psi x$, $\psi y$, $\phi x$, $\phi y$, $\phi z$, $\theta x$ and $\theta y$ in order to estimate an incident direction (for example, expressed by $\theta x$ and $\theta y$) of an electron beam. In other words, it is a case where the equation to express the geometric relationship between the observed amount (for example, a tilt angle of an edge of a calibrator) and an output variable (an incident direction of an electron beam) can not be described without using parameters such as $\psi x$, $\psi y$, $\phi x$, $\phi y$, $\phi z$, $\theta x$ and $\theta y$. However, at least the shape and tilt direction of a calibrator should be estimated or known for estimating a tilt angle.

The methods used to estimate the positional relationship of an incident direction of a wafer surface, pyramid and electron beam are not limited to ones using the parameters $\psi x$, $\psi Y$, $\phi x$, $\phi y$, $\phi z$, $\theta x$ and $\theta y$. In addition, though an example using a pyramidal specimen as a calibrator is used in the foregoing explanations, it is also possible to uniquely define a tilt direction with calibrators other than pyramidal specimens.

Tilt Angle Estimation Method 1 (Basic Principle: Single Image, an Image Only)

The method to estimate a beam tilt angle by processing a beam tilt image will now be explained. FIG. 6(*a*) shows a pattern diagram of a SEM image of a concave pyramid observed from above. The changes in the beam tilt angle are reflected in the appearance of a pyramid. In other words, the length and tilt angle of the segments 301 to 308 of the pyramid shown in FIG. 6(*a*) change depending on the beam tilt angle.

Definition of Output Parameters

Consequently, a parameter expressing a beam tilt angle can be estimated by detecting a part or all of the segments 301 to 308 from an image and measuring the length and tilt angle. After that, a parameter to be estimated is called an "output parameter". In this case, it is a parameter to express a beam tilt angle and is given by the parameters $\theta x$ and $\theta y$. A output parameter group is expressed as an output parameter vector $$U=(\theta x, \theta y)^T.$$

Definition of Reference Parameters

The length or tilt angle of the pyramid also changes depending on the changes of each parameter expressing the tilt angles of wafer surfaces or pyramids and image distortions, etc. In other words, each parameter expressing the tilt angle of a wafer surface or pyramid and image distortions, etc should be selectively estimated as required in order to obtain an output parameter. These parameters that must be estimated in order to obtain an output parameter are called a "reference parameter" hereinafter. In this case, they are parameters to express a tilt angle of a wafer surface or a pyramid and image distortion. For example, they are given with the parameters $\psi x$, $\psi y$, $\phi x$, $\phi y$, $\phi z$. A reference parameter group is expressed as a reference parameter vector $V=(\psi x, \psi y, \phi x, \phi y, \phi z)^T$. A reference parameter is added or deleted as required. In other words, if the slope $\psi x$ and $\psi y$ of a wafer surface need not be estimated for estimating an output parameter, the slopes $\psi x$ and $\psi y$ are deleted from the reference parameter. Likewise, an image distortion needs to be estimated for estimating an output parameter, and so a parameter describing the image distortion is added to the reference parameter. The case where the slope $\psi x$ and $\psi y$ of a wafer surface need not be estimated is a case where an estimation parameter is obtained by using only the information of the slope of the segments 301 to 304 on an observed image in FIG. 6(*a*) as an observed amount. That is because a change in the slope of a wafer surface will affect the slope of the segments 305 to 308 in FIG. 6(*a*), however, it does not affect the slope of the segments 301 to 304.

The output parameter and reference parameter are collectively called an "estimation parameter". An estimation parameter group is expressed as a estimation parameter vector $T=(U^T, V^T)^T$.

3.2.3 A Method to Estimate an Estimation Parameter

FIG. 10 is a conceptual diagram of a method used to estimate an estimation parameter. The image 401 is processed by extracting segments from a SEM image or a reflective electron image of a calibrator that is imaged, or the SEM image or a reflective electron image. Combinations of varied values are assigned to each element of an estimation parameter vector in order to obtain an estimation parameter vector T (405, FIG. 10) at the time of imaging the calibrator 401, simulating what calibrator is observed in each combination. If the combination of varied values of each element is expressed as $T^{(1)}$, $T^{(2)}$, ..., $T^{(n-1)}$, $T^{(n)}$, $T^{(n+1)}$, by using the right upper superscripts, the shape of a calibrator that is observed when the values of an estimation parameter vector are $T^{(n-1)}$, $T^{(n)}$, $T^{(n+1)}$ (406 to 408 respectively in FIG. 10) is given by 402 to 404, respectively, by use of a geometric equation.

The correlation between the simulated calibrator shape and the calibrator shape in an image is calculated. Therefore, the estimation parameter vector T (n) (407) in the most similar simulation shape (403 in FIG. 10) corresponds to the estimation parameter vector 405 in an image that is taken. The methods to calculate the estimation parameter vector where a taken image and simulation image correlate with each other at maximum by changing the estimation parameter vector include, as described above, a method to sequentially assign values and a method to analytically obtain a solution by the least-square method, etc. In addition, the methods for a correlated calculation include a method based on the degree of similarity of the length or tilt angle of a part of or all of the segments 301 to 308 in a taken image and simulation image as shown in FIG. 6(*a*), or the coordinate values of a part of or all of the vertexes $P_0$ to $P_4$ shown in FIG. 6(*a*).

In the explanation mentioned above, the output parameter to be finally estimated is the beam tilt angle. The case where a stage tilt angle and body tube tilt angle are estimated from the stage tilt method and body tube tilt method is also the same. In other words, it is possible to calculate an estimation parameter vector where a taken image and simulation image match each other at maximum if a geometric shape change on an image of a calibrator to any given estimation parameter can be simulated. For example, in the stage tilt method, an output parameter serving as an observational direction (an incident direction of an electron beam to a specimen) may be a tilt angle of a calibrator because the calibrator mounted on the stage tilts while the stage tilts. A tilt angle of a calibrator is obtained by determining an estimation parameter vector T, as shown in FIG. 10, in the same manner as the estimation of a beam tilt angle. In this case, estimation parameter vector T includes a tilt angle of a calibrator as an output parameter. If an observational direction where a semiconductor wafer surface is perpendicularly observed is defined as a stage tilt angle 0°, when a tilt angle of a pyramid relative to the observational direction where a semiconductor wafer surface is perpendicularly observed is $\phi_0$, and a tilt angle of a pyramid relative to the observational direction in any given tilt angle is $\phi$, the stage tilt angle is given by $\phi - \phi_0$.

In addition, "a sequence to estimate a beam tilt angle using two images, a top-down image and a beam tilt image", as mentioned below, includes a step to estimate a tilt angle of a calibrator by using a top-down image. Also, in the step, a tilt angle of a calibrator is estimated as an output parameter.

Tilt Angle Estimation Method 2 (Variation Two Images or in Combination with Other Measuring Means)

Varied sequences are assumed for the methods used to estimate the estimation parameters. They include, other than a method to estimate all estimation parameters at one time from a piece of observed image, (1) a sequence to partially estimate an estimation parameter by dividing them, (2) a sequence to use multiple pieces of observed images, (3) a sequence to estimate a part or all of estimation parameters by means other than images and to use the results of estimations or a sequence to combine (1) to (3). For example, (a) a sequence to estimate a beam tilt angle using a top-down image and a beam tilt image, and (b) a sequence to measure the slope of a wafer surface and the slope of a calibrator by a measuring means other than image processing and to estimate a beam tilt angle by using the measurement results will now be explained sequentially.

Methods to Estimate an Estimation Parameter-Variation 1

(a) A Sequence to Estimate a Beam Tilt Angle Using Two Images, a Top-Down Image and a Beam Tilt Image In some cases, it is difficult to uniquely obtain an estimation parameter from a piece of beam tilt image. For example, if a tilted calibrator is observed on an image, it is sometimes difficult to determine whether it is caused by the tilt angle 209 of a calibrator or a slope 210 of an incident direction of an electron beam because of problems concerning image quality or resolution, or insufficient information obtained from an image compared to the number of estimation parameters.

FIG. 11 shows a sequence used to estimate an estimation parameter by using two pieces of image.

In this sequence, an image (called a "beam tilt image") of a calibrator produced by setting a tilt angle in the direction to be observed and an image (referred to as "top-down image" hereinafter) where a calibrator is observed with a beam tilt angle set to 0° are obtained, an actual tilt angle in a top-down image taken with a tilt angle set to 0° is assumed to be 0°, a tilt angle of a calibrator is estimated independently by using a top-down image, and a beam tilt angle is estimated independently by using a beam tilt image.

First, a top-down image is taken (step 501), a tilt angle and a rotation angle of a calibrator, and, if required, other reference parameters are calculated by using the top-down image (step 502). In the step 502, a tilt angle of a calibrator is calculated with a beam tilt angle that is known (0°). Therefore, the uniqueness of a solution is higher than the case where all estimation parameters are calculated at one time and the calculation is easier. Then, a beam tilt image is taken after setting a beam tilt image in a direction to be observed (step 503). The true value of the beam tilt angle and, if required, other reference parameters are estimated (step 504). In the step 504, a tilt angle is calculated with a tilt angle of a calibrator that is known (a value calculated in the step 502 is used)

making the calculation easier than the step 502. There are several variations of order estimatable in which a specific estimation parameter is calculated. As shown above, the number of estimation parameters is reduced by dividing the parameters to be estimated, raising the uniqueness of solutions.

The calculations are performed here with a beam tilt angle 0° in a top-down image. However, in some cases, the actual beam tilt angle is deviated from 0° in a top-down image taken with a beam tilt angle 0°. In those cases, the size of the deviation may affect the estimation accuracy of a beam tilt angle after that. In an optical system originally designed to obtain a top-down image, a higher setting accuracy is requested in a beam tilt angle near the top-down. Therefore., estimating an actual beam tilt angle which is 0° in a top-down image, estimating a tilt angle by using a tilt angle of a calibrator estimated from the top-down image as an input value can reduce the error when estimating a tilt angle more than using a tilt angle of a calibrator estimated from an observed image with a tilt angle set to an angle tilted over 0° as an input value.

In the stereo view detailed below, when a three-dimensional space is reconstructed by using the tilt images $I_L$, $I_R$ obtained respectively at the beam tilt angle set values $\theta_L$, $\theta_R$, it is expected that the deviation $\Delta\theta^0$ from the beam tilt angle 0° in the top-down image little affects the three-dimensional space reconstruction error. That is because, if a tilt angle is estimated in the tilt images $I_L$, $I_R$ respectively by using a tilt angle of a calibrator obtained from a top-down image by the sequence as an input value (the estimated values are Est[$\theta$L], Est[$\theta$R] respectively), the deviation of Est[$\theta$L], Est[$\theta$R] from the true value is almost the same as $\Delta\theta^0$. Therefore, the relative angle error of Est[$\theta$L], Est[$\theta$R] is small and the error in the three-dimensional reconstructed shape by stereo view is also small.

The calculations after that are performed with a beam tilt angle in a top-down image set to 0°. In the same manner, an estimation parameter can be obtained by assigning an approximate value the parameter similar with a parameter supposed to have no large error which is known. The methods include, for example, a method in which the slope of a wafer surface is set to 0° approximately, etc.

Methods to Estimate an Estimation Parameter-Variation 2

(b) A sequence to measure the slope of wafer surface and a calibrator by means other than image processing and to estimate a beam tilt angle by using the measurement results Methods to measure an estimation parameter or the relationship between estimation parameters (relative values, etc) include a method which employs image processing and a distance measuring method by using an SPM or objective lens focused focal point, etc. An example of the method to estimate a beam tilt angle by using image processing in a selective or integrated manner or other measuring means will now be explained.

FIG. 12 shows a beam tilt angle estimation method using an SPM, objective lens focused focal point and image processing. First, a specimen is mounted on the SPM before a SEM observation. The specimen surface in area, including the wafer surface 602 and calibrator 604, is measured. The distance data 606 of the specimen surface obtained is described based on the coordinate system 601 set in the SPM. Angles made by planes constituting the specimen surface are obtained by multi-plane approximating the distance data 606 by local plane assignment. Therefore, the relative angle between the tilt direction 603 of the wafer surface and the tilt direction 605 of the calibrator can be calculated.

Then, the specimen is mounted on the SEM and the slope direction 608 of the wafer surface 602 is estimated based on the distance measurement result by the objective lens focused focal point. The distance measurement by the objective lens focused focal point is a method used to estimate the distance to an objective to be observed when an actual objective is observed by calculating the relationship between the control current of the objective lens and the distance to the objective when it is focused on in advance. A slope direction 608 is estimated with a plane normal line by assigning the planes, etc to the distance data based on the objective lens focused focal point. The slope direction 608 of the wafer surface 602 obtained is described based on the coordinate system 607 set in a SEM.

The relative angle between the slope direction 608 of the wafer surface in the coordinate system 607 and the slope direction 609 of a calibrator is equivalent to the relative angle between the slope direction 603 of a wafer surface in the coordinate system 601 already measured and the slope direction 605 of a calibrator. The slope direction 609 in the coordinate system 607 can be calculated by using the slope direction 608 of the wafer surface and the relative angle. Assuming that the slope direction of a calibrator serving as one of the reference parameters has already been calculated, the beam tilt angle 612 to the coordinate system 607 serving as an output parameter is calculated by image processing. The accuracy to estimate the depth by the focused focal point of an objective lens is about several parts of the focal depth. Therefore, when the slope of a wafer surface is measured, the measurement accuracy must be secured by calculating the slope based on large distance data (e.g., end to end of a specimen on a wafer).

Thus, in some methods, all estimation parameters are not measured by image processing, but are measured by using measuring means such as an SPM or focused focal point of an objective lens in a selective or integrated manner considering the measurement accuracy and usability of each measuring means. There are varied variations considered other than the combinations described above (e.g., all data other than the relative angle between the slope direction 608 of a wafer surface and the slope direction 609 of a calibrator is estimated by image processing). Further, it is not required to measure the positional relationship between a wafer surface and a calibrator every time an estimation parameter is obtained because it is invariable once measured.

Imaging Sequence (Including Imaging of Objective Image)—Including a Method to Correct an Estimated Value Accompanying Changes in Imaging Conditions The imaging sequence of a calibrator including imaging of a semiconductor pattern (refereed to as an "objective pattern" hereinafter) in any given coordinate system to be observed on a semiconductor wafer with a SEM will now be explained. The imaging sequences for a calibrator and objective pattern, including (a) a sequence to image an objective pattern after imaging a calibrator (FIG. 13(*a*)), (b) a sequence to image a calibrator after imaging an objective pattern (FIG. 13(*b*)) and (c) a sequence to image a calibrator off-line (FIG. 14) will now be explained sequentially. In the sequences (a) and (b), an objective pattern and a calibrator are imaged alternately. Therefore, a calibrator specimen 1319 is mounted on the position 705 in FIG. 7(*a*) where attachments and removals of a semiconductor wafer are not required. In the sequence (c), a calibrator specimen 1319 is mounted on the position 704 or 705 in FIG. 7(*a*).

Imaging Sequence-Variation 1

(a) A Sequence to Image an Objective Pattern After Imaging a Calibrator (FIG. 13(a))

This is a sequence, in which a calibrator is first imaged with any given tilt angle set, where the setting is not changed basically (it may be changed when a tilt angle is calibrated), then, an objective pattern is imaged. When there are hysteresis characteristics between a tilt angle set value and an actual tilt angle, even if any given tilt angle set value is changed to a different set value temporarily and it is returned to the original tilt angle set value, the actual tilt angles in the former and latter tilt angle set value may not be the same. This sequence avoids the risk that a tilt angle estimated by a calibrator can not be used in an analysis of an observed image of an objective pattern.

This sequence will now be explained with reference to FIG. 13(a). First, a semiconductor wafer is mounted on a SEM (step 800). Then, an imaging point is set on a specimen on which a calibrator is formed (step 801). A tilt angle is changed into any give set value (step 802). There is no problem if the order of the steps 801 and 802 is reversed. After setting a tilt angle, a calibrator is imaged in the step 804. If required, the imaging conditions are changed in the step 803 before imaging the calibrator. If required, multiple calibrators are imaged in multiple imaging conditions with the loop 810.

In the loop 810, multiple calibrators are imaged while changing the imaging conditions. In the loop 810, a calibrator is imaged by the combination of imaging conditions required for estimating a tilt angle in an objective pattern image group to be imaged in the loop 811 later. Further, it is expected that the reliability of estimated values is improved by estimating a tilt angle from multiple calibrator images. Therefore, if a tilt angle in the objective pattern image group can be estimated by the observed images of a calibrator obtained by one imaging condition, the loop 801 is not used. The changes in the imaging conditions include stage movements, image shifts (movements of visual field due to a changed irradiation position of an electron beam), magnification changes, focus changes, astigmatic corrections, etc. In imaging, an imaging point may be changed, or the image may be enlarged or reduced. At that moment, the focus may be changed or astigmatic corrections are performed to obtain good images. Further, if required, an estimated value of a tilt angle is calculated from a calibrator image obtained in the step 804 and the tilt angle is calibrated in the step 805 in order to eliminate the deviations between the estimated value of the tilt angle and the set value of the tilt angle.

Figure 15:
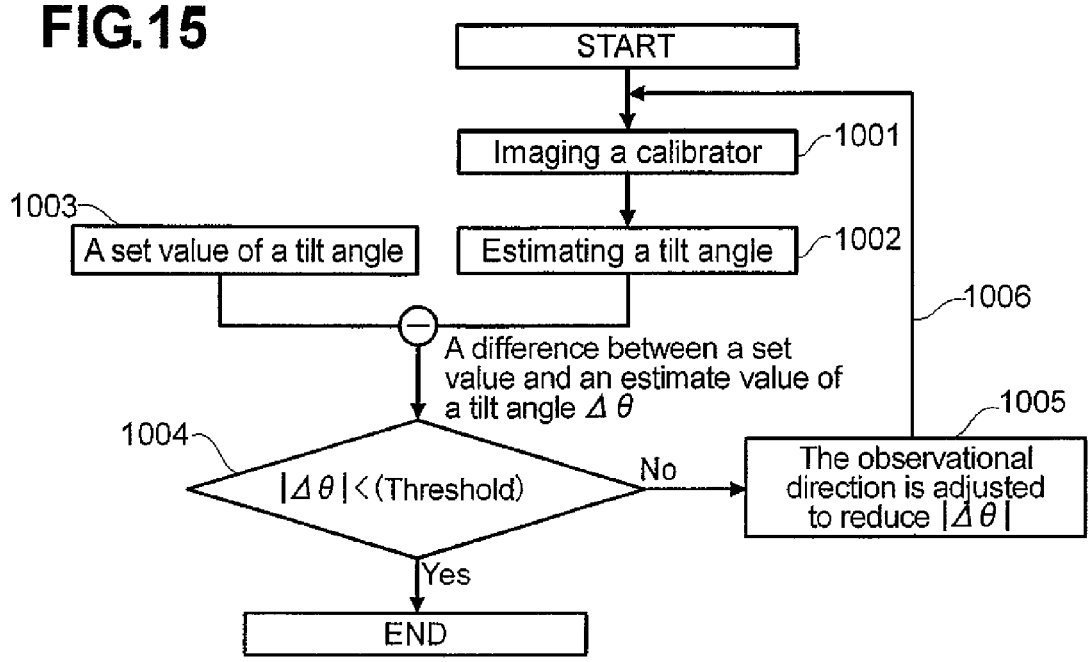
FIG. 15 is a flowchart showing a method used to calibrate a tilt angle.

An observed image can be obtained in the set observational direction in the step 808 by performing the calibration. The calibration method for tilt angles will be detailed later (FIG. 15). If required, the calibrator imaging (step 804), tilt angle estimation, tilt angle calibration (step 805) are repeated in the loop 810 until an estimated value of a tilt angle does not deviate from a set value of a tilt angle. After correcting a tilt angle (step 805), a calibrator is imaged again (step 804). Confirm that there is no deviation between an estimated value and a set value of a tilt angle. If the step 805 is skipped to image an objective pattern, the set value of a tilt angle is the same between the step 804 and the step 808. If the calibrator is not imaged again, the set value of the tilt angle is different between the steps 804 and 808. However, if a tilt angle on imaging an objective pattern can be estimated within an allowable error required for the analysis of the object pattern later, there is no problem.

Then, the imaging position is moved to the semiconductor wafer (step 806). An objective pattern is imaged in the step 808. If required, the imaging conditions are changed before imaging an objective pattern in the step 807. If required, multiple objective patterns are imaged by the loop 811.

Imaging Sequence-Variation 2

(b) A Sequence to Image a Calibrator After Imaging an Objective Pattern (FIG. 13(b))

In this sequence, any given tilt angle is set, an objective pattern is imaged in any given imaging condition, and then, a calibrator is imaged with the tilt angle setting unchanged to estimate a tilt angle. This sequence has an advantage in that the imaging conditions in observing the objective pattern can be determined based on the imaging conditions in observing the objective pattern by observing a calibrator after imaging an objective pattern. In other words, the tilt angle may be changed if the imaging conditions are changed. Therefore, a tilt angle when imaging an objective pattern can be estimated more correctly by imaging a calibrator in the imaging conditions similar to the observations of the objective pattern.

This sequence will be explained with reference to FIG. 13(b). First, a semiconductor wafer is mounted on a SEM (step 813). Then, an imaging is set on the semiconductor wafer on which an objective pattern is formed (step 814) and the tilt angle is changed into any given set value (step 815). There is no problem if the order of the steps 814 and 815 is reversed. After setting a tilt angle, an objective pattern is imaged in the step 816. If required, the imaging conditions are changed in the step 815 before imaging the objective pattern. At the same time, if required, multiple objective patterns are imaged in multiple imaging conditions with the loop 821.

Then, the imaging position is moved on a specimen on which a calibrator is formed (step 817). The calibrator is imaged in the step 819. Before imaging the calibrator, if required, the imaging conditions are changed in the step 818. At the same time, in the loop 822, images of the calibrator are taken in multiple conditions required for estimating a tilt angle when imaging an objective pattern in the step 816.

In FIG. 13(a) and FIG. 13(b), the imaging condition change (step 803, 807, 814, 817) and imaging position change (step 801, 806, 814, 817) are separated. The imaging condition change includes the stage movement and image shift. This means a stage movement or an image shift between calibrators or objective patterns. Meanwhile, the imaging position change means a stage movement between a calibrator and an objective pattern. If the tilt angle when setting any given tilt angle shown in FIG. 11 is estimated by the combination of the tilt image and top-down image in setting the tilt angle of a calibrator the imaging of an object pattern (step 808 and 816) with the tilt angle set to 0° (top-down) is skipped.

Imaging Sequence-Variation 3

Figure 14:
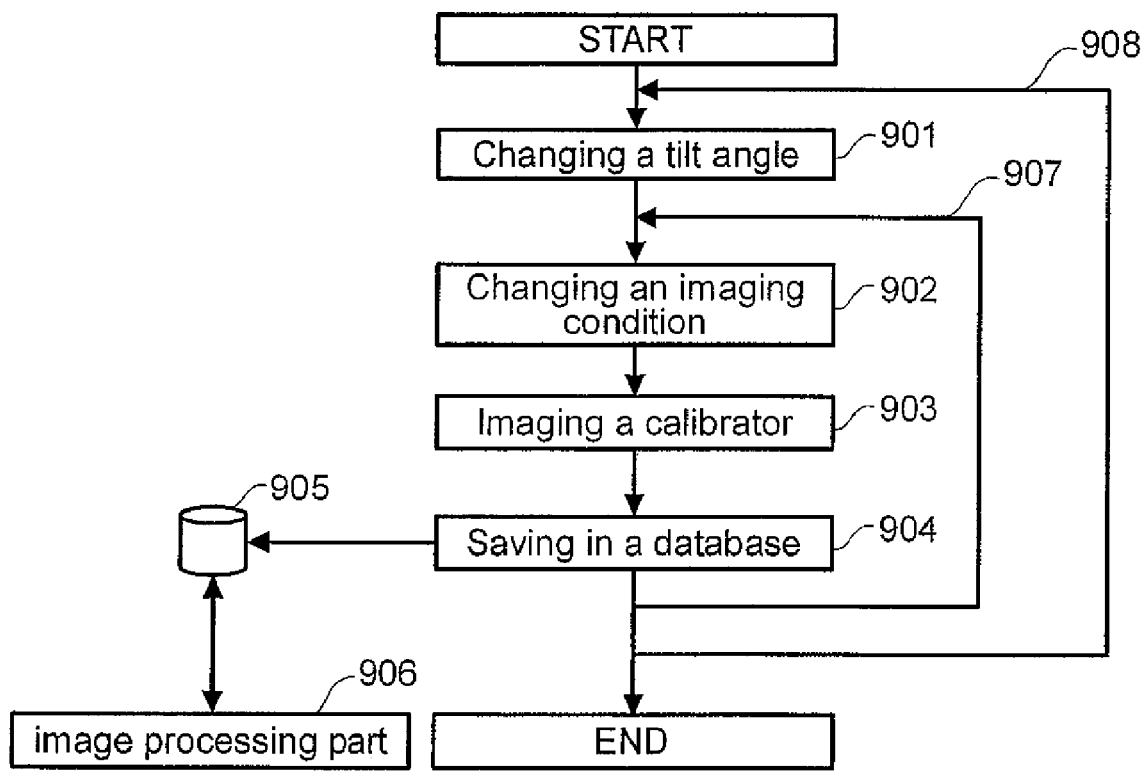
FIG. 14 is a flowchart showing a sequence used to save an image of a calibrator, and to refer the information of the database to estimate an incident direction of an electron beam.

(c) A Sequence to Image a Calibrator Off-Line (FIG. 14)

In this sequence a calibrator is imaged by the combination of a tilt angle and imaging conditions to be required for estimating a tilt angle before inputting a semiconductor wafer or imaging an objective pattern, and the image group and the tilt angle estimated by the image group is saved in a data base with the imaging conditions. The tilt angle in an objective pattern imaged in any given imaging conditions later can be estimated by the data base.

This sequence will be explained with reference to FIG. 13(c). Calibrators at multiple areas are imaged by the combination of a tilt angle to be imaged and imaging conditions (The tilt angle change, imaging condition change and imaging are performed in the steps 901, 902, and 903, respectively). The image of a calibrator is saved in a data base 905. If required, an estimated value of a tilt angle is calculated in any given tilt angle set value or imaging conditions in the image processing part 902 by using an image group saved in the data base. The estimated value is saved in the data base 905 in the form of a library. A tilt angle in an objective pattern imaged in any given imaging conditions later can be estimated from the data base by using the data base. Even if an image of a calibrator imaged in the same conditions as the tilt angle set value or imaging conditions in imaging an objective pattern is not saved in the data base, an estimated value of a tilt angle in imaging the objective pattern can be calculated by an interpolation, etc from an estimated value of a tilt angle imaged by other conditions in the data base.

Figure 13:
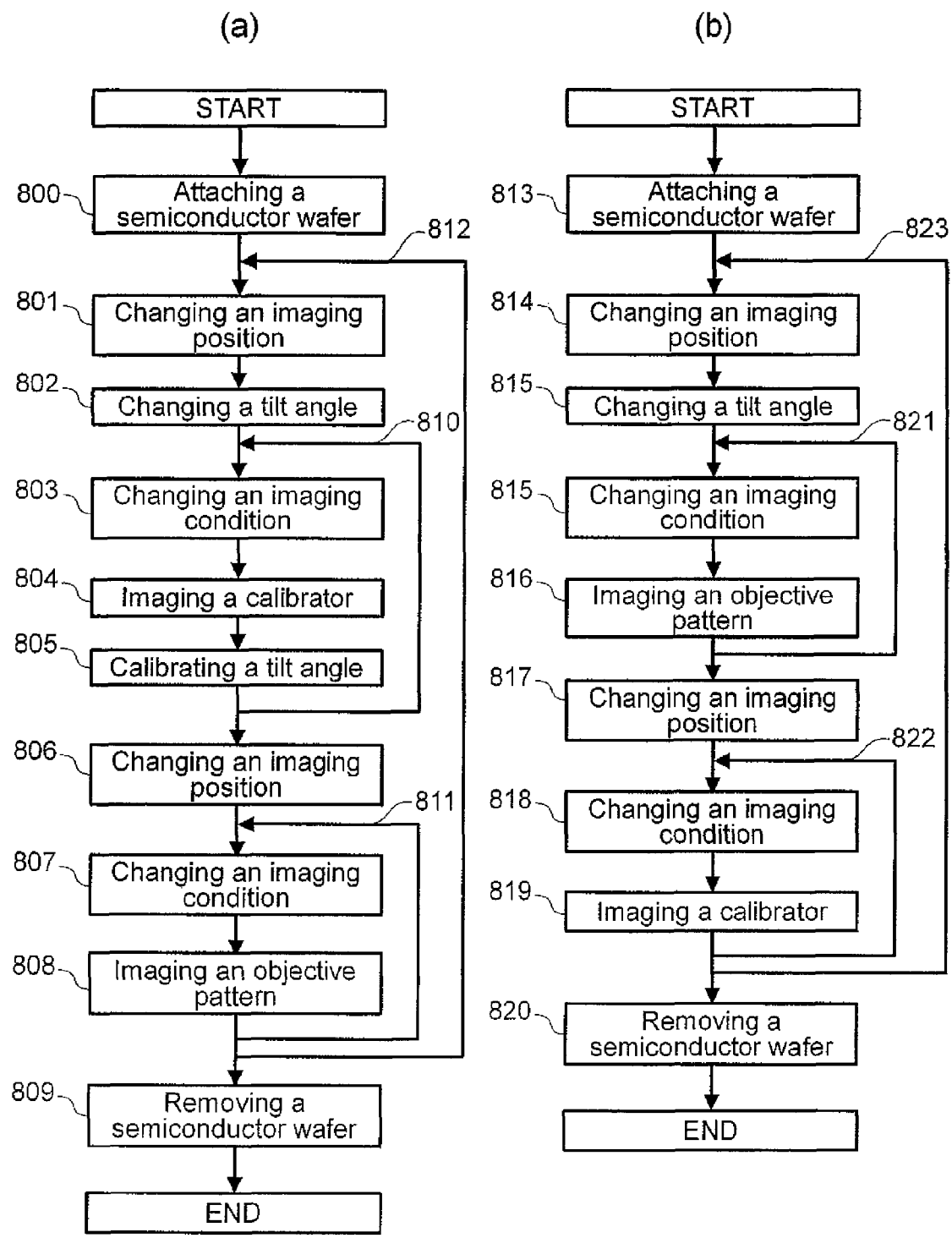
FIGS. 13(a) and 13(b) are flowcharts showing a sequence to image a target pattern and a calibrator.

In imaging a calibrator in the three imaging sequences shown in FIG. 13(*a*) and FIG. 13(*b*) and FIG. 14, the deviations in the estimated values of the observational direction caused by the individual difference and image noises can be reduced by observing single calibrators or multiple different calibrators disposed sequentially, estimating an observational direction in each image and using an average or median in the observational direction.

Estimated Value Correction Accompanying Imaging Condition Change

The actual tilt angle may be different between the objective pattern imaging and the calibrator imaging even if the set tilt angle is not changed between them. Therefore, the tilt angle can be estimated by estimating the variation of the tilt angle accompanying the imaging condition changes, and adding the variation to the estimated tilt value in imaging a calibrator.

The method to calculate the variation of the tilt angle accompanying the changes in the imaging conditions will now be explained.

The variation of a tilt angle due to a stage movement, image shift or magnification change among the changes in the imaging conditions can be estimated from the distribution of the tilt angle in the semiconductor wafer plane (e.g., estimated from a tilt angel of a calibrator mounted at the position 704 in FIG. 7) or distribution of tilt angles in the visual field (e.g., estimated from a tilt angle in a calibrator 706 in FIG. 7). Especially, with regard to the image shift, the changes in the incident direction of an electron beam due to the shift of an electron beam can be estimated by a geometric calculation of an optical system. In addition, the variation in the tilt angle due to changes in the focus among the changes in the imaging conditions can be estimated by experimentally or analytically calculating the relationship between the control current value of an objective lens and the tilt angle. In other words, the focus is changed by changing the control current of an objective lens. Therefore, a tilt angle can be estimated by using a control current of an objective lens in observing an objective pattern if the relationship between the control current and tilt angle of the objective lens is obtained.

Use of Estimated Results (Tilt Angle Calibration, 3D Reconstruction, GUI Display, Etc)

The uses of an estimated tilt angle in observations or measurements of an observed image will now be explained.

Calibration of Tilt Angles

A tilt angle can be calibrated with an estimated value of a tilt angle with a calibrator and a set value, and the actual tilt of a tilt angle can be matched with each other (corresponding to the step 808 in FIG. 13).

FIG. 15 shows a sequence used to calibrate a tilt angle. First, any given tilt angle to be observed is set. Then, an image of a calibrator is obtained (step 1001, corresponding to the step 804 in FIG. 13(*a*)). An estimated tilt angle value is calculated from the image of a calibrator (step 1002, corresponding to the determination of an estimation parameter T shown in FIG. 10 mentioned above). The difference $\Delta\theta$ between the estimated value and set value of the tilt angle is calculated. If the absolute value of $\Delta\theta$ is larger than the threshold set in advance (condition 1004), the deflection of an electron beam is changed in the beam tilt method or the slope of the stage is changed in the stage tilt method in such a manner the absolute value of the $\Delta\theta$ is reduced (step 1005). After that, the calibrator is observed and a tilt angle is estimated by the loop 1006. The re-calculated $\Delta\theta$ is judged to confirm whether to meet the condition 1004 is met. This process is repeated until the condition 1004 is met to make the estimated value of the tilt angle convert to the set value.

CD Measurement or Shape Index Calculation

By the measurement of a critical dimension or the other dimensions corresponding to any part of semiconductor patterns in a top-down view or tilt view, as disclosed in the Japanese Published Unexamined Patent Application No. 2000-022617, it is possible to estimate the semiconductor pattern 3D shape or calculate indices which have high correlation with the pattern 3D shape. The critical dimension and the other dimensions are called "various CDs" in all hereinafter.

However, a setting error of the tilt angle leads to the measurement error of various CDs.

The present calibration method makes it possible to estimate a reliable measurement value of various CDs by following either of two disposals.

(1) To correct measured various CD values by using estimated tilt angle
(2) To measure various CDs in the adjusted image with a desired tilt angle (setting error of tilt angle is corrected by the calibration)

Figure 19:
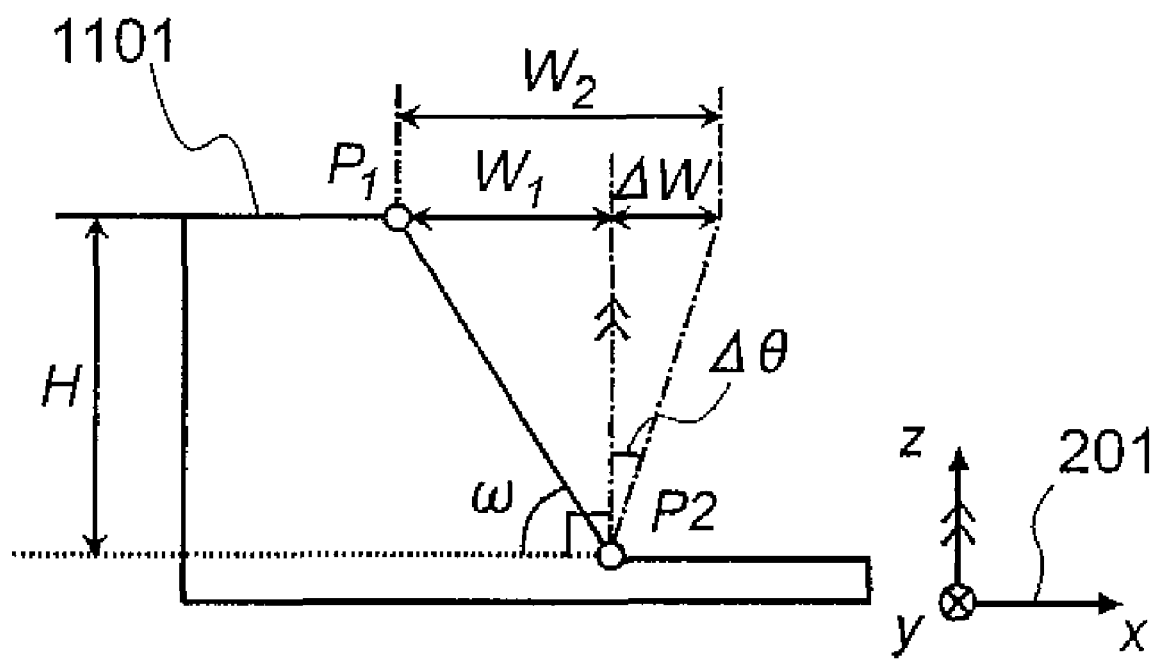
FIG. 19 shows a partial cross-section of a pattern.

FIG. 19 shows, as an example of the disposals (1) abovementioned, a method to calculate correct side wall length $W_1$ (observation length in top-down view) in the case of estimation of side wall angle ω.

If the height of step H is known, the side wall angle ω is given by $\tan^{-1}(H/W_1)$.

However, if the observation direction includes an angle error □θ, the side wall length also includes a length error □W and side wall length becomes $W_2=W_1$□W.

The present calibration method can estimate the angle error E 0 and calculate the correct side wall length $W_1=W_2-$□W=$W_2$−Htan(□θ).

The disposal can be also applicable similarly to the case of the other part of semiconductor pattern and tilt angle variations.

3D Reconstruction

In a 3D profile reconstruction by using an observed image of an objective pattern from multiple directions, a higher reconstruction accuracy is obtained by (1) using a tilt angle estimated with a calibrator as an input value of an observational direction or (2) using an observed image and a set value of a tilt angle of an objective pattern imaged in the observational direction equivalent to the set value by calibrating the tilt angle and a set value of a tilt angle as an input value.

Figure 16:
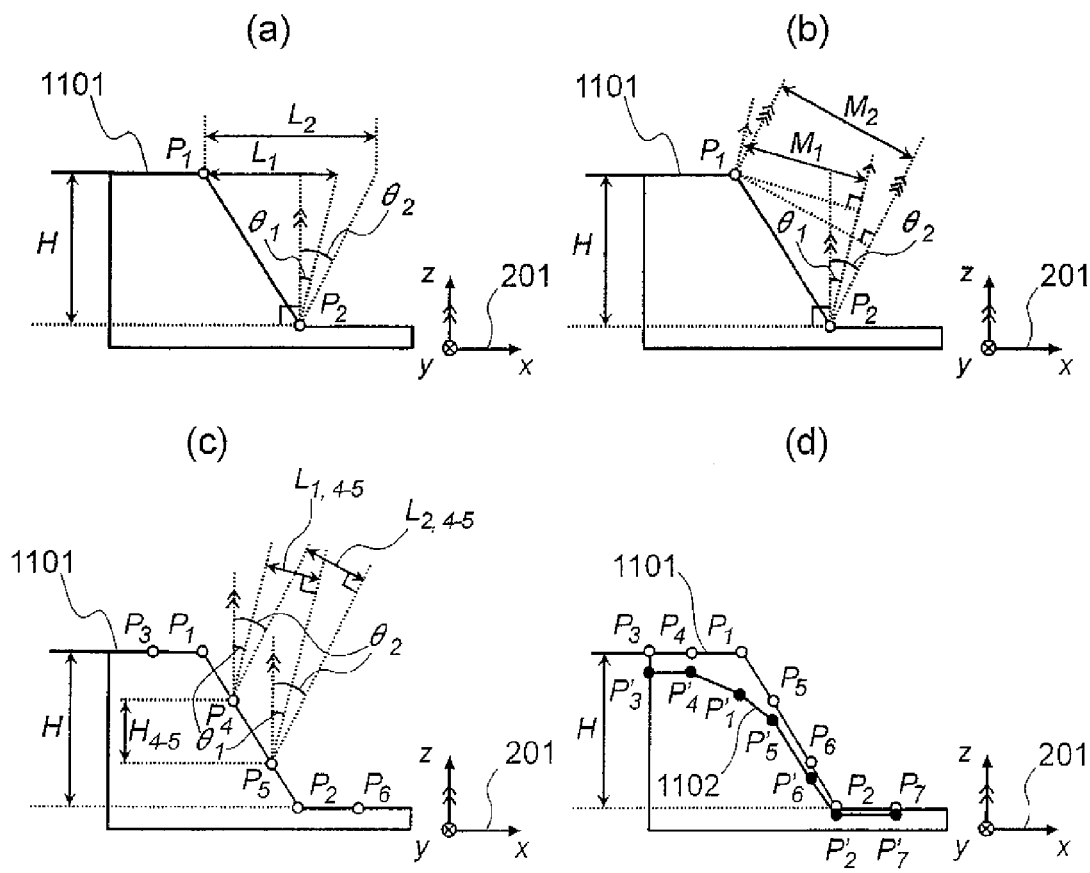
FIG. 16(a) to FIG. 16(d) are partial cross-sections of a pattern to illustrate a principle used to measure a height by a stereovision.
Figure 17:
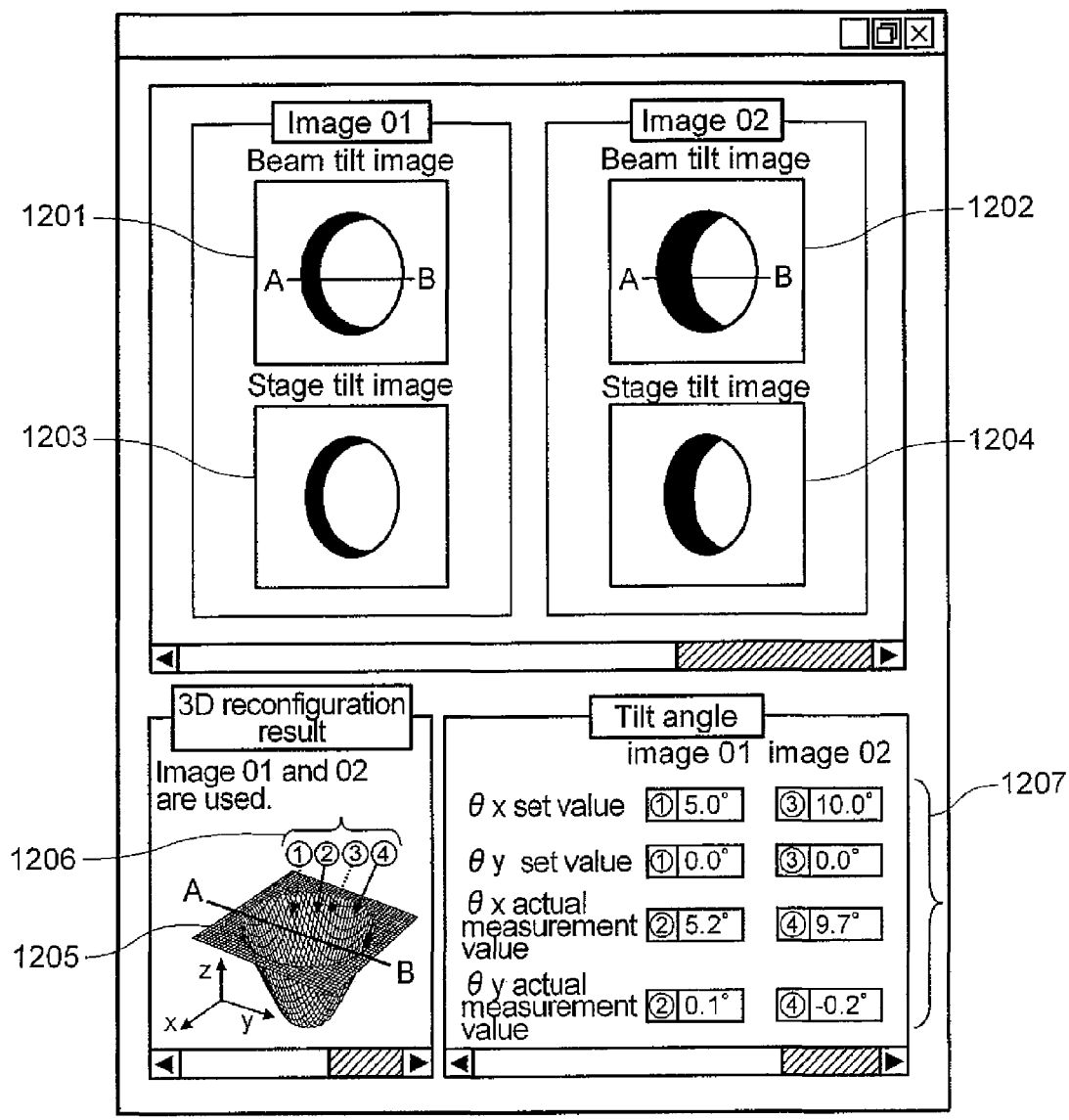
FIGS. 17(a) and 17(b) are diagrams which show an embodiment of a GUI to display an estimated result of a tilt angle.
Figure 17:
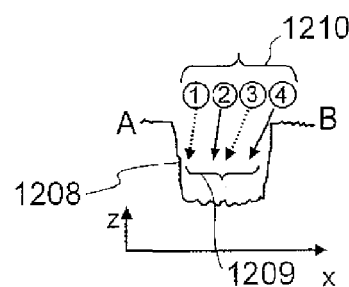

FIG. 16 shows, as an example of an algorithm used to reconfigure a 3D profile, a method to calculate the step (height) between the two points $P_1$-$P_2$ in the section 1101 of a measuring object. For example, the absolute coordinate system 201 in a SEM is used as a standard for the direction to measure the step. The height in the z-axis direction of the absolute coordinate system 201 is measured as a step. In FIG. 16(*a*), $L_1$ and $L_2$ are the distances between the two points $P_1$-$P_2$ on an image observed from above with beam tilt angles $\theta_1$ and $\theta_2$, respectively. The step H between the two points $P_1$-$P_2$ is given by $H=\{(L_1-L_2)\cdot\cos\theta_1\cdot\cos\theta_2\}/\sin(\theta_1-\theta_2)$ by using $L_1$, $L_2$, $\theta_1$ and $\theta_2$ through a geometric calculation.

In the same way, in FIG. 16(*b*), $M_1$ and $M_2$ are the distances between the two points $P_1$-$P_2$ observed from above with a stage tilt angles $\theta_1$ and $\theta_2$, respectively in a image. The step H between the two points $P_1$-$P_2$ is given by $H=(M_1 \cos\theta_2 - M_2 \cos\theta_1)/\sin(\theta_1-\theta_2)$ by using $M_1$, $M_2$, $\theta_1$, $\theta_2$ through a geometric calculation. The input errors of the tilt angles $\theta_1$ and $\theta_2$ affect the 3D profile reconstruction both in the beam tilt observation and stage tilt observation. Therefore, the reconstruction accuracy can be improved by correctly estimating and inputting the observational direction in an observed image.

FIG. 16(a) and FIG. 16(b) show an example of calculations of the step H between the points $P_1$-$P_2$. The irregularities on the surface of an object pattern can be measured more precisely irrespective of the outside or inside of the points $P_1$-$P_2$. FIG. 16(c) shows a method used to measure the points $P_1$-$P_7$ on the surface of an objective pattern by using a beam tilt image. For example, the step $H_{5-6}$ between the points $P_5$-$P_6$ is given by $H_{5-6}=\{(L_{1,\,5-6}-L_{2,\,5-6}) \cdot \cos\theta_1 \cdot \cos\theta_2\}/\sin(\theta_1-\theta_2)$ in the same manner as the case shown in FIG. 16(a) by using the distances $L_{1,\,5-6}$ and $L_{2,\,5-6}$ between the two points observed from above with beam tilt angles $\theta_1$ and $\theta_2$, respectively. The quality of a semiconductor pattern and the semiconductor process variations can be checked and controlled by measuring the height, line width and side wall slope angle of the objective pattern, and subtle pattern shape such as rounded corners from the measurement results obtained.

In FIG. 16(d), the points $P_1$-$P_7$ (indicated with the white circles in FIG. 16(d)) on the objective pattern surface 1101 obtained from the design data, etc and the measurement points $P'_1$-$P'_7$ of the height of the point $P_1$-$P_7$ measured by each tilt image (indicated with the black circles in FIG. 16(d), 1102 is the multi-point approximate shape of the black circles connected to one another on the objective pattern surface) are overlapped. In this example, it is clear that the step is lower than the design value in the shape (the shape of the measurement data) of the objective pattern completed and the corner near the point P1 is rounded. Thus, the objective pattern status can be evaluated by displaying the shape of the design data and measurement results set out or overlapped, or displaying the shapes, such as the height and roundness of the corners, etc digitized. In addition, for example, as shown in FIG. 17(a), the 3D shape measurement results 1205 can be obtained by two-dimensionally measuring the multi-points on an objective pattern surface in the direction of the x- and y-axis of the absolute coordinate system 201.

GUI Display

An estimated value of the actual tilt angle can be displayed on a GUI or a beam tilt image can be converted to a stage tilt image for display by using an estimated value of a tilt angle by a calibrator.

FIG. 17(a) shows an example of a GUI (Graphic User Interface) to display the estimation results of an observed image and tilt angle. The image displays 1201 and 1202 are the beam tilt images with the set value of the observational direction 5° and 100° respectively (referred to as "image 01" and "image 02" respectively hereinafter). The image displays 1203 and 1204 are the stage tilt images estimated and displayed at the estimated value of the tilt angle of the set value or the tilt angle by the calibration from the beam tilt images 1201 and 1202. A stage tilt image can be estimated from a beam tilt image and an observational direction to be displayed even if a stage tilt image is not observed actually.

It is difficult to interpret a beam tilt image obtained by deflecting an electron beam intuitively because it is geometrically different from an oblique perspective image seen with the naked eyes of a human. Therefore, converting an image into a stage tilt image which is comparable to an observation by a human obtained by tilting a stage is effective for analyses with the human eye. Further, in the case where a stage tilt image is observed, it is possible to reversely convert it into a beam tilt image to be displayed. Still further, in the image displays 1201-1204, an image with the distortion corrected can be displayed by using the results of the image distortion estimation, an example of which is shown in FIG. 7(c).

1205 denotes a 3D display of a 3D profile estimated from an observed image. The 3D profile can be displayed in any given observational direction. 1206 denotes vectors three-dimensionally expressing the set value of the observational direction in the image 01 and 02, and the estimated values of the observational direction using a calibrator. The components of the vector (the set value and estimated value of the tilt angle in the x- and y-direction) are displayed at 1207. Further, the 3D profile and the observational direction can be two-dimensionally displayed as shown in FIG. 17(b) at 1208 and 1209, respectively. In FIG. 17(b), 1208 and 1209 denote the estimated 3D profile and the observational direction projected on the x-z plane as an example, respectively. (1)-(4) in 1206, 1207 and 1209 correspond to one another. Further, the errors between the set value and estimated value in an observational direction, an observed image of a calibrator and a slope direction of a calibrator and wafer can be also displayed.

As shown above, any give combination of a beam tilt image of an objective pattern (1201, 1202), a stage tilt image (1203, 1204), a 3D profile of an estimated objective pattern (1205), a 3D display of an observational direction(1206), a two-dimensional display of an observational direction (1209 or 1102 in FIG. 16(d)), a digitized display of an observational direction (1207) and a design shape of an objective pattern obtained from design data, etc (1101 in FIG. 16(d)) can be displayed on the same GUI.

In the above-described examples of the tilts observed mainly in the beam tilt method and the pyramidal specimens used as calibrators, methods to arrange the calibrators, methods to detect the geometric deformations in the observed images, methods to estimate the observational directions, sequences to estimate the taken images and observational directions have been explained. However, the present invention is not limited to those examples. The present invention can be applied to other methods to observe tilts and calibrators in the same manner.

In accordance with the present invention, correct observations and measurements can be performed by using the tilt observation images of the objective patterns and correct estimated values of observational directions. Further, even in the SEM devices with hysteresis characteristics (when the actual tilt angle deviates every time a tilt angle is set even if the same value is set to the tilt angle) or with a bad repeatability, a tilt angle can be observed and measured in a more accurate and repeatable fashion by estimating and calibrating the tilt angle. Further, even when the same specimen is observed with different SEM devices, the difference in the tilt angles by the different SEM devices is estimated, the difference between devices due to the difference between the tilt angles is corrected, and the same measurement results can be obtained. The measurements include, for example, measurements of dimensions, such as line widths and contact hole diameters, and the above-mentioned 3D profile measurements. The variations of the semiconductor processes can be effectively detected by the measurement values with a high accuracy. Further, in the case where an objective pattern with a surface tilt angle more than 90°, called an "inverse tapered shape", is measured (there is an area that can not be measured when observed from just above), the tilt observation is especially effective. The observation and measurement methods in accordance with the present invention are very important for the analyses with a high degree of accuracy.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for observing a specimen, comprising the steps of:
    irradiating and scanning a convergent electron beam, from a desired direction, on a surface of a calibration substrate on which a pattern with a known shape is formed, and obtaining a beam SEM image of the pattern formed on the calibration substrate;
    calculating an actual direction of the electron beam irradiated on the surface of the calibration substrate by use of the information about an apparent geometric deformation of the known shape on the SEM image; and
    wherein the pattern with the known shape formed on the calibration substrate has a crystal plane formed by anisotropic chemical etching.

2. A method for observing a specimen according to the claim 1, wherein the pattern with the known shape is a quadrangular pyramid and a tilt angle of each plane of the quadrangular pyramid is known.

3. A method for observing a specimen according to claim 1, wherein the pattern with the known shape is a quadrangular pyramid and each plane of the quadrangular pyramid is (111) crystal plane or a plane in a direction equivalent to the (111) crystal plane.

4. A method for observing a specimen according to claim 1, wherein multiple patterns with the known shape are arranged on the calibration substrate.

5. A method for observing a specimen according to claim 1, wherein a direction of the convergent electron beam is changed by tilting the electron beam.

6. A method for observing a specimen according to claim 1, wherein a direction of the convergent electron beam is changed by tilting the calibration substrate.

7. A method for observing a specimen according to claim 1, wherein a direction of the convergent electron beam is changed by tilting the electron optical system.

8. A method for observing a specimen according to claim 1, wherein the calculating of the actual direction of the electron beam includes correction of SEM image distortion.

9. A device for observing a specimen comprising:
    a table which carries a specimen having a calibration substrate;
    a SEM imager which obtains a SEM image in a desired direction including a vertical or oblique direction relative to a surface of the calibration substrate, and which detects a secondary electron or reflective electron generated from the specimen by irradiation with an electron beam;
    an image processing unit which processes a SEM image obtained by the SEM imager;
    a calculator which calculates an actual direction of the electron beam irradiated on the surface of the calibration substrate on which a pattern with a known shape is formed by using information about an apparent geometric deformation of the known shape on the SEM image; and
    a controller which controls the SEM imager;
    wherein the pattern with the known shape formed on the calibration substrate has a crystal plane formed by anisotropic chemical etching.

10. A device for observing a specimen according to claim 9, wherein the pattern with the known shape is a quadrangular pyramid and a tilt angle of each plane of the quadrangular pyramid is known.

11. A device for observing a specimen according to claim 9, wherein the pattern with the known shape is a quadrangular pyramid and each plane of the quadrangular pyramid is (111) crystal plane or a plane in a direction equivalent to the (111) crystal plane.

12. A device for observing a specimen according to claim 9, wherein multiple patterns with the known shape are arranged on the calibration substrate.

13. A device for observing a specimen according to claim 9, wherein the SEM imager is adjusted by tilting the table.

14. A device for observing a specimen according to claim 9, wherein the SEM imager is adjusted by tilting the table.

15. A device for observing a specimen according to claim 9, wherein the SEM imager is adjusted by tilting the electron optical system.

16. A device for observing a specimen according to claim 9, wherein the controller further controls the image processing unit to correct a distortion of the SEM image obtained by the SEM imager.

17. A device for observing a specimen comprising:
    a table which carries a specimen;
    a SEM imager which obtains a SEM image of the specimen by irradiating and scanning an electron beam on a surface of the specimen and detecting a secondary electron or reflected electron generated from the specimen;
    an image processing unit which processes a SEM image obtained by the SEM imager;
    a display screen which displays the SEM image or an image processed by the image processing unit;
    a calculator which calculates a direction of the electron beam incident on a surface of a calibration substrate forming at least a part of the specimen and on which a crystal plane pattern is formed; and
    a controller which controls the SEM images to adjust the direction of the electron beam incident on the surface of the surface of the calibration substrate by using information of the calculated direction.

18. A device for observing a specimen according to claim 17, wherein the crystal plane pattern has a quadrangular pyramid shape and tilt angle of each plane of the quadrangular pyramid is known.

19. A device for observing a specimen according to claim 17, wherein the crystal plane pattern has a quadrangular pyramid shape and each plane of the quadrangular pyramid is (11) crystal plane or a plane in a direction equivalent to the (111) crystal plane.

20. A device for observing a specimen according to claim 17, wherein the controller further controls the image processing unit to correct a distortion of the SEM image obtained by the SEM imager.

21. A device for observing a specimen according to claim 17, wherein the image processing unit processes the SEM image obtained by the SEM image obtainer which is controlled by the controller and obtains dimension information of a pattern formed on the specimen.

22. The method for observing a specimen according to the claim 1, further comprising the step of:
    adjusting the actual direction of the electron beam to the desired direction by using information of the calculated direction.

23. The device for observing a specimen according to claim 9, wherein the controller adjusts the actual direction of the electron beam to the desired direction by using information of the calculated direction.

* * * * *